United States Patent
Nakayama et al.

(10) Patent No.: US 9,897,790 B2
(45) Date of Patent: Feb. 20, 2018

(54) STRUCTURED ILLUMINATION DEVICE AND STRUCTURED ILLUMINATION MICROSCOPE DEVICE

(71) Applicant: NIKON CORPORATION, Tokyo (JP)

(72) Inventors: Hiroaki Nakayama, Kawasaki (JP); Yumiko Ouchi, Yokohama (JP)

(73) Assignee: NIKON CORPORATION, Tokyo (JP)

( * ) Notice: Subject to any disclaimer, the term of this patent is extended or adjusted under 35 U.S.C. 154(b) by 0 days.

(21) Appl. No.: 14/996,717

(22) Filed: Jan. 15, 2016

(65) Prior Publication Data

US 2016/0131885 A1 May 12, 2016

Related U.S. Application Data

(63) Continuation of application No. PCT/JP2014/002855, filed on May 29, 2014.

(30) Foreign Application Priority Data

Jul. 17, 2013 (JP) .................................. 2013-148730

(51) Int. Cl.
*F21V 9/16* (2006.01)
*G02B 21/06* (2006.01)
(Continued)

(52) U.S. Cl.
CPC ............. *G02B 21/06* (2013.01); *G01N 21/64* (2013.01); *G01N 21/6428* (2013.01);
(Continued)

(58) Field of Classification Search
CPC .................. G02B 21/0032; G02B 21/0064; G02B 21/06; G02B 21/16; G02B 21/02;
(Continued)

(56) References Cited

U.S. PATENT DOCUMENTS 5,424,552 A * 6/1995 Tsuji .................... G03F 7/70241
250/548
RE38,307 E 11/2003 Gustafsson et al.
(Continued)

FOREIGN PATENT DOCUMENTS

WO 2006/109448 A1 10/2006

OTHER PUBLICATIONS

Kner et al., "Super-Resolution Video Microscopy of Live Cells by Structured Illumination," Nature Methods, May 2009, vol. 6, No. 5, pp. 339-342 and 2 pages of online methods.
(Continued)

*Primary Examiner* — Taeho Jo
(74) *Attorney, Agent, or Firm* — Oliff PLC

(57) ABSTRACT

A structured illumination device includes: a diffraction unit that diffracts light beams of a plurality of wavelengths that are emitted simultaneously or sequentially by a light source into a plurality of diffracted beams; and an optical system that forms interference fringes on a surface of a sample using the plurality of diffracted beams diffracted by the diffraction unit, the optical system including a first optical system and a second optical system that focuses the plurality of diffracted beams at positions on or near a pupil plane of the first optical system, and a magnification characteristic $dY(\lambda)$ of the second optical system satisfying the condition of $(fo \cdot nw - af\lambda/P) \leq dY(\lambda) \leq (fo \cdot NA - af\lambda/P)$, where $a=1$ (for M=1, 2) or $a=2$ (for M=3).

18 Claims, 24 Drawing Sheets

(51) Int. Cl.
  *G01N 21/64* (2006.01)
  *G02B 21/00* (2006.01)
  *G02B 21/36* (2006.01)
  *G02B 27/58* (2006.01)
  *G02B 21/16* (2006.01)

(52) U.S. Cl.
  CPC ..... *G02B 21/0032* (2013.01); *G02B 21/0076* (2013.01); *G02B 21/16* (2013.01); *G02B 21/367* (2013.01); *G02B 27/58* (2013.01); *G01N 2021/6439* (2013.01); *G01N 2201/063* (2013.01); *G01N 2201/0638* (2013.01)

(58) Field of Classification Search
  CPC .. G02B 21/26; G02B 26/0808; G02B 5/1814; G02B 6/2931; G01N 2021/6421; G01N 21/64; G01N 2201/0612; G01N 2201/0638; G01N 2201/0675; G01N 2201/068; G01N 15/1436; G01N 2021/6463; G01N 2201/062; G01N 2201/063; G01N 27/44721
  USPC ...................................... 250/458.1
  See application file for complete search history.

(56) References Cited

U.S. PATENT DOCUMENTS

| | | | |
|---|---|---|---|
| 8,115,806 B2 | 2/2012 | Osawa et al. | |
| 9,395,522 B2* | 7/2016 | Ono | G02B 15/177 |
| 2001/0009476 A1* | 7/2001 | Iizuka | G02B 27/1086 359/566 |
| 2002/0008863 A1* | 1/2002 | Taniguchi | G03F 7/701 355/55 |
| 2005/0174495 A1* | 8/2005 | Itoh | G02B 13/0095 348/758 |
| 2008/0130103 A1* | 6/2008 | Hara | A61B 5/0059 359/369 |
| 2008/0204682 A1* | 8/2008 | Uehara | G03F 7/70258 355/46 |
| 2009/0268280 A1* | 10/2009 | Osawa | G02B 21/0032 359/363 |
| 2010/0141750 A1* | 6/2010 | Osawa | G02B 21/06 348/79 |
| 2010/0188960 A1* | 7/2010 | Yasui | G11B 7/1353 369/112.23 |
| 2012/0008194 A1* | 1/2012 | Mizuta | G02B 21/025 359/377 |
| 2013/0228704 A1* | 9/2013 | Kalkbrenner | G01N 21/64 250/459.1 |
| 2013/0329121 A1* | 12/2013 | Ono | G02B 15/177 348/345 |

OTHER PUBLICATIONS

Sep. 2, 2014 International Search Report issued in International Patent Application No. PCT/JP2014/002855.
Jan. 19, 2016 International Preliminary Report on Patentability issued in International Patent Application No. PCT/JP2014/002855.
May 23, 2017 Office Action issued in Japanese Patent Application No. 2015-527148.

* cited by examiner

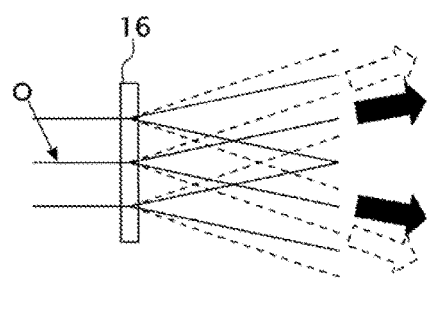
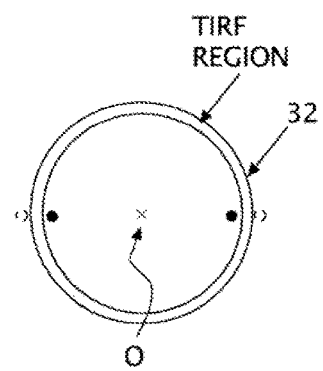
FIG. 8A                FIG. 8B
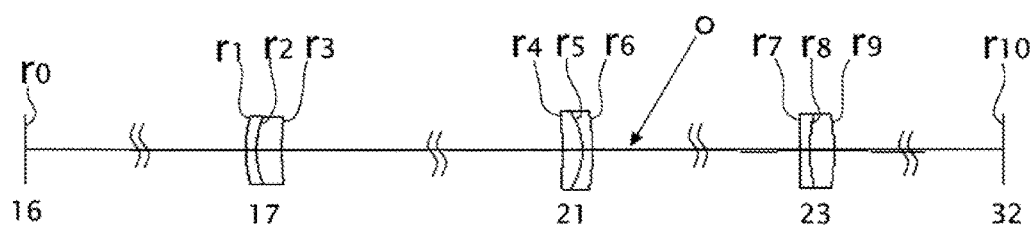
FIG. 9

| No | r | d | nd | νd |
|---|---|---|---|---|
| 0 | 0 | 116.7 | | |
| 1 | 28.042 | 2.0 | 1.80810 | 22.76 |
| 2 | 17.429 | 5.0 | 1.60311 | 60.68 |
| 3 | 60.570 | 265.8 | | |
| 4 | −126.069 | 4.0 | 1.59270 | 35.30 |
| 5 | −14.292 | 2.0 | 1.60311 | 60.68 |
| 6 | −50.754 | 297.6 | | |
| 7 | 629.867 | 2.0 | 1.80810 | 22.76 |
| 8 | 33.533 | 5.0 | 1.56907 | 71.31 |
| 9 | −46.308 | 140.1 | | |
| 10 | 0 | 0.0 | | |

FIG. 11

| FOCAL LENGTH fo OF OBJECTIVE LENS [mm] | | | | 2 | | |
|---|---|---|---|---|---|---|
| NUMERICAL APERTURE NA OF OBJECTIVE LENS | | | | 1.49 | | |
| FOCAL LENGTH f OF LIGHT-COLLECTING OPTICAL SYSTEM [mm] | | | | 120 | | |
| PITCH P OF DIFFRACTION GRATING [μm] | | | | 50 | | |
| REFRACTIVE INDEX OF WATER | | | | 1.33 | | |
| REFERENCE WAVELENGTH λ0 [nm] | | | | 588 | | |
| WAVELENGTH λ [nm] | 405 | 436 | 486 | 588 | 656 | |
| CHROMATIC ABERRATION OF MAGNIFICATION dY [mm] | 1.01 | 0.70 | 0.37 | 0.00 | −0.17 | |
| LEFT SIDE OF CONDITIONAL EXPRESSION (2) [mm] | 0.72 | 0.57 | 0.33 | −0.16 | −0.49 | |
| RIGHT SIDE OF CONDITIONAL EXPRESSION (2) [mm] | 1.04 | 0.89 | 0.65 | 0.16 | −0.17 | |

FIG. 12

| WAVELENGTH λ [nm] | 405 | 436 | 486 | 588 | 656 |
|---|---|---|---|---|---|
| AXIAL CHROMATIC ABERRATION | 0.586 | 0.280 | 0.182 | 0.000 | −0.119 |

FIG. 13

| No | r | d | nd | νd |
|---|---|---|---|---|
| 0 | 0 | 90.3 | | |
| 1 | 36.969 | 5.0 | 1.49782 | 82.56 |
| 2 | -33.926 | 2.0 | 1.61720 | 54.00 |
| 3 | -132.605 | 13.2 | | |
| 4 | 107.739 | 5.0 | 1.71300 | 53.89 |
| 5 | -41.495 | 2.0 | 1.72342 | 37.94 |
| 6 | 37.216 | 2.1 | | |
| 7 | 44.636 | 5.0 | 1.49782 | 82.56 |
| 8 | -24.966 | 2.0 | 1.62004 | 36.24 |
| 9 | 166.395 | 145.2 | | |
| 10 | -89.049 | 2.0 | 1.60311 | 60.68 |
| 11 | 17.251 | 5.0 | 1.59270 | 35.30 |
| 12 | -34.170 | 3.0 | | |
| 13 | -25.897 | 2.0 | 1.74320 | 49.32 |
| 14 | 14.424 | 5.0 | 1.74077 | 27.79 |
| 15 | -32.412 | 123.1 | | |
| 16 | -84.428 | 2.0 | 1.69895 | 30.13 |
| 17 | 49.111 | 5.0 | 1.49782 | 82.56 |
| 18 | -34.507 | 274.3 | | |
| 19 | 101.370 | 2.0 | 1.61340 | 44.27 |
| 20 | 46.958 | 5.0 | 1.49782 | 82.56 |
| 21 | -159.550 | 147.0 | | |
| 22 | 0 | 0.0 | | |

| | | | | | |
|---|---|---|---|---|---|
| FOCAL LENGTH fo OF OBJECTIVE LENS [mm] | | | | | 2 |
| NUMERICAL APERTURE NA OF OBJECTIVE LENS | | | | | 1.49 |
| FOCAL LENGTH f OF LIGHT-COLLECTING OPTICAL SYSTEM [mm] | | | | | 120 |
| PITCH P OF DIFFRACTION GRATING [μm] | | | | | 50 |
| REFRACTIVE INDEX OF WATER | | | | | 1.33 |
| REFERENCE WAVELENGTH λ0 [nm] | | | | | 588 |
| WAVELENGTH λ [nm] | 405 | 436 | 486 | 588 | 656 |
| CHROMATIC ABERRATION OF MAGNIFICATION dY [mm] | 1.03 | 0.71 | 0.38 | 0 | −0.17 |
| LEFT SIDE OF CONDITIONAL EXPRESSION (2) [mm] | 0.72 | 0.57 | 0.33 | −0.16 | −0.49 |
| RIGHT SIDE OF CONDITIONAL EXPRESSION (2) [mm] | 1.04 | 0.89 | 0.65 | 0.16 | −0.17 |

FIG. 19

| WAVELENGTH λ [nm] | 405 | 436 | 486 | 588 | 656 |
|---|---|---|---|---|---|
| AXIAL CHROMATIC ABERRATION | 0.019 | −0.105 | −0.032 | 0.000 | −0.067 |

| No | r | d | nd | νd |
|---|---|---|---|---|
| 0 | 0 | 116.7 | | |
| 1 | 186.000 | 2.0 | 1.74951 | 35.33 |
| 2 | 58.613 | 5.0 | 1.59240 | 68.33 |
| 3 | -84.200 | 265.8 | | |
| 4 | 229.330 | 4.0 | 1.49782 | 82.56 |
| 5 | -42.030 | 2.0 | 1.61266 | 44.46 |
| 6 | -84.520 | 297.6 | | |
| 7 | 101.370 | 2.0 | 1.61340 | 44.27 |
| 8 | 46.958 | 5.0 | 1.49782 | 82.56 |
| 9 | -159.550 | 147.0 | | |
| 10 | 0 | 0.0 | | |

FIG. 20

| WAVELENGTH λ [nm] | 405 | 436 | 486 | 588 | 656 |
|---|---|---|---|---|---|
| CHROMATIC ABERRATION OF MAGNIFICATION dY [mm] | 0.0031 | 0.0002 | -0.0012 | 0 | 0.0014 |

FIG. 21

| WAVELENGTH λ [nm] | 405 | 436 | 486 | 588 | 656 |
|---|---|---|---|---|---|
| AXIAL CHROMATIC ABERRATION | 0.184 | -0.092 | -0.192 | 0.000 | 0.180 |

FIG. 22

| No | r | d | nd | νd |
|---|---|---|---|---|
| 0 | 0 | 0 | | |
| 1 | 0 | 2 | 1.458467 | 67.70 |
| 2 | 0 | 103.2 | | |
| 3 | 40.066 | 2.6 | 1.497820 | 82.56 |
| 4 | -68.073 | 1.8 | 1.805180 | 25.45 |
| 5 | -385.631 | 8.5 | | |
| 6 | -30.602 | 1.3 | 1.755200 | 27.57 |
| 7 | 42.274 | 3 | 1.640000 | 60.20 |
| 8 | -36.348 | 12.7 | | |
| 9 | 239.422 | 1.8 | 1.846660 | 23.80 |
| 10 | 39.051 | 2.6 | 1.497820 | 82.56 |
| 11 | -29.752 | 80.23 | | |
| 12 | 0 | 0 | | |

| WAVELENGTH λ [nm] | 405 | 436 | 486 |
|---|---|---|---|
| PITCH P OF DIFFRACTION GRATING [μm] | | 29.8 | |
| a | | 2 | |
| DIFFRACTION ANGLE OF + FIRST-ORDER DIFFRACTED LIGHT [rad] | 0.027181 | 0.029262 | 0.032617 |
| FOCAL LENGTH OF LENS 317 [mm] | | 88.2 | |
| DISTANCE FROM OPTICAL AXIS TO FOCUSED LIGHT SPOTS ON LIGHT BEAM SELECTOR 18 PLANE [mm] | 2.88 | 2.85 | 2.88 |
| FOCAL LENGTH OF LENS 321 [mm] | | 130 | |
| FOCAL LENGTH OF LENS 323 [mm] | | 130 | |
| PROJECTION MAGNIFICATION FROM LIGHT BEAM SELECTOR 18 TO PUPIL PLANE 32 | | 1 | |
| DISTANCE FROM OPTICAL AXIS TO FOCUSED LIGHT SPOTS ON PUPIL PLANE 32 [mm] | 2.88 | 2.85 | 2.88 |

FIG. 27

| | | |
|---|---|---|
| FOCAL LENGTH fo OF OBJECTIVE LENS [mm] | 2 | |
| NUMERICAL APERTURE NA OF OBJECTIVE LENS | 1.49 | |
| FOCAL LENGTH OF LIGHT-COLLECTING OPTICAL SYSTEM (LENSES 317, 321, AND 323) [mm] | 88.2 | |
| PITCH P OF DIFFRACTION GRATING [μm] | 29.8 | |
| a | 2 | |
| REFRACTIVE INDEX OF WATER | 1.33 | |
| REFERENCE WAVELENGTH λ0 [nm] | 486 | |
| WAVELENGTH λ [nm] | 405 | 436 |
| CHROMATIC ABERRATION OF MAGNIFICATION dY [mm] | 0.582 | 0.299 |
| LEFT SIDE OF CONDITIONAL EXPRESSION (2) [mm] | 0.263 | 0.079 |
| RIGHT SIDE OF CONDITIONAL EXPRESSION (2) [mm] | 0.583 | 0.399 |

FIG. 28

| WAVELENGTH λ [nm] | 405 | 436 |
|---|---|---|
| AXIAL CHROMATIC ABERRATION OF LENS 317 AT LIGHT BEAM SELECTOR 18 (TRACED FORWARDS) | 13.91 | 6.92 |
| AXIAL CHROMATIC ABERRATION OF LENS 317 AT LIGHT BEAM SPLITTER 14 (TRACED BACKWARDS) | 30.58 | 13.96 |

FIG. 29

STRUCTURED ILLUMINATION DEVICE AND STRUCTURED ILLUMINATION MICROSCOPE DEVICE

CROSS REFERENCE TO THE RELATED APPLICATIONS

This application is a continuation application of International Application PCT/JP2014/002855, filed May 29, 2014, designating the U.S., and claims the benefit of priority from Japanese Patent Application No. 2013-148730, filed on Jul. 17, 2013, the entire contents of which are incorporated herein by reference.

BACKGROUND

1. Field

The present invention relates to a structured illumination device and a structured illumination microscope device.

2. Description of the Related Art

In the fields of observation and measurement of samples (specimens), structured illumination microscopes (SIM) have been proposed as one way of achieving resolutions that exceed the performance of objective lenses (see Patent Document 1: US Reissued Patent Application Publication No. 38307, for example). In a structured illumination microscope, the sample is illuminated with spatially modulated illumination light (structured illumination light) and an image (a modulated image) of the sample is captured. Then, the modulation components contained in the modulated image are removed (that is, the image is demodulated) in order to produce a super-resolution image (a demodulated image).

In the structured illumination microscope disclosed in the Patent Document 1 in particular, a light beam emitted from a light source is split into a plurality of light beams using a diffraction grating or the like. These light beams interfere in the area around the specimen, forming interference fringes which are used as the structured illumination light.

SUMMARY

Like in other microscopes, there may be a need to change the wavelength of the light source in such a structured illumination microscope in order to observe a sample that has been dyed with a plurality of pigments that are excited by different wavelengths of light.

However, changing the wavelength of the light source in the structured illumination microscope changes the diffraction angle of the diffraction grating, thereby changing the distance of the illumination light spots from the radius of the pupil of the objective lens, and in some cases, making it no longer possible to achieve the desired super-resolution effect at all.

The present invention was made in light of the foregoing and aims to provide a structured illumination device and a structured illumination microscope device that make it possible to achieve the desired super-resolution effect when using each of a plurality of wavelengths.

A structured illumination device according to one aspect of the present invention includes: a diffraction unit that diffracts light beams of a plurality of wavelengths that are emitted simultaneously or sequentially by a light source into a plurality of diffracted beams; and an optical system that forms interference fringes on a surface of a sample using the plurality of diffracted beams diffracted by the diffraction unit, the optical system including a first optical system and a second optical system that focuses the plurality of diffracted beams at positions on or near a pupil plane of the first optical system, and a magnification characteristic $dY(\lambda)$ of the second optical system satisfying the following condition for each wavelength of the plurality of wavelengths.

$$(fo \cdot nw - af\lambda/P) \leq dY(\lambda) \leq (fo \cdot NA - af\lambda/P),$$

where a=1 (for M=1, 2) or a=2 (for M=3)

Here, M is a number of directions in which the diffraction unit has a periodic structure, $\lambda$ is any wavelength of the plurality of wavelengths, $dY(\lambda)$ is a difference between an image height $2f \cdot \lambda_0/P$ where $\lambda_0$ is a reference wavelength for the plurality of wavelengths and an image height $2f \cdot \lambda/P$ where $\lambda$ is any wavelength of the plurality of wavelengths, fo is a focal length of the first optical system for the wavelength $\lambda$, f is a focal length of the second optical system for the wavelength $\lambda$, P is a pitch of the diffraction unit, NA is a numerical aperture of the first optical system, and nw is a refractive index of the wavelength $\lambda$ of the sample.

Here, "magnification characteristics" refers to changes in the distance from the optical axis to the light beams that pass through the second optical system when the wavelength is changed. These magnification characteristics include the chromatic aberration of magnification that remains in the second optical system after correcting the aberration thereof as well as the chromatic aberration of magnification intentionally given to the second optical system.

A structured illumination microscope device according to one aspect of the present invention includes: the structured illumination device according to one aspect of the present invention: and an imaging optical system that uses light beams observed from the sample when modulated by the interference fringes to form an image on a light detector.

Furthermore, a structured illumination device according to one aspect of the present invention includes: a diffraction unit that diffracts light beams of a plurality of wavelengths that are emitted simultaneously or sequentially by a light source into a plurality of diffracted beams; and an optical system that forms interference fringes on a surface of a sample using the plurality of diffracted beams diffracted by the diffraction unit, the optical system including a first optical system and a second optical system that focuses the plurality of diffracted beams at positions on or near a pupil plane of the first optical system, and a magnification characteristic $dY(\lambda)$ of the second optical system satisfying the following condition for each wavelength of the plurality of wavelengths.

$$(0.75fo \cdot NA - af\lambda/P) \leq dY(\lambda) \leq (fo \cdot NA - af\lambda/P),$$

where a=1 (for M=1, 2) or a=2 (for M=3)

Here, M is a number of directions in which the diffraction unit has a periodic structure, $\lambda$ is any wavelength of the plurality of wavelengths, $dY(\lambda)$ is a difference between an image height $2f \cdot \lambda_0/P$ where $\lambda_0$ is a reference wavelength for the plurality of wavelengths and an image height $2f \cdot \lambda/P$ where $\lambda$ is any wavelength of the plurality of wavelengths, fo is a focal length of the first optical system for the wavelength $\lambda$, f is a focal length of the second optical system for the wavelength $\lambda$, P is a pitch of the diffraction unit, and NA is a numerical aperture of the first optical system.

BRIEF DESCRIPTION OF DRAWINGS

FIGS. 8A and 8B illustrate how the diffraction angle and the distance from an optical axis O to focused light spots change when the wavelength used λ is switched.

FIG. 9 illustrates the configuration of a light-collecting optical system (lenses 17, 21, and 23).

FIG. 11 is a table of lens data for the light-collecting optical system (the lenses 17, 21, and 23) of Embodiment 1.

FIG. 12 is a correspondence table of conditions for the light-collecting optical system (the lenses 17, 21, and 23) of Embodiment 1.

FIG. 13 is table of the axial chromatic aberration of the light-collecting optical system (the lenses 17, 21, and 23) of Embodiment 1.

FIG. 17 is a table of lens data for the TIRF-SIM mode light-collecting optical system (the lenses 17A, 21A, and 23) of Embodiment 2.

FIG. 18 is a correspondence table of conditions for the TIRF-SIM mode light-collecting optical system (the lenses 17A, 21A, and 23) of Embodiment 2.

FIG. 19 is a table of the axial chromatic aberration of the TIRF-SIM mode light-collecting optical system (the lenses 17A, 21A, and 23) of Embodiment 2.

FIG. 20 is a table of lens data for the TIRF mode light-collecting optical system (the lenses 17B, 21B, and 23) of Embodiment 2.

FIG. 21 is a table of the chromatic aberration of magnification of the TIRF mode light-collecting optical system (the lenses 17B, 21B, and 23) of Embodiment 2.

FIG. 22 is a table of the axial chromatic aberration of the TIRF mode light-collecting optical system (the lenses 17B, 21B, and 23) of Embodiment 2.

FIG. 27 is a table that gives the distance from the optical axis O to the light beams on the plane in which the beam selection member 20 is arranged (the pupil conjugate plane) for each wavelength of light, the focal lengths of a lens 321 and a field lens 323, the projection magnification from the plane in which the beam selection member 20 is arranged to a pupil plane 32, and the distance from the optical axis O to the focused light spots formed on the pupil plane 32 of an objective lens 31.

FIG. 28 is a correspondence table of conditions for a light-collecting optical system (lenses 317, 321, and 323) of Embodiment 3.

FIG. 29 shows the axial chromatic aberration of the lens 317 at the plane in which the beam selection member 20 is arranged (the pupil conjugate plane) and the axial chromatic aberration of the lens 317 at the plane in which the light beam splitter 14 is arranged (as calculated by tracing the light beams backwards).

DETAILED DESCRIPTION OF THE EMBODIMENTS

Embodiment 1

Next, a structured illumination microscope device according to Embodiment 1 of the present invention will be described.

Figure 1:
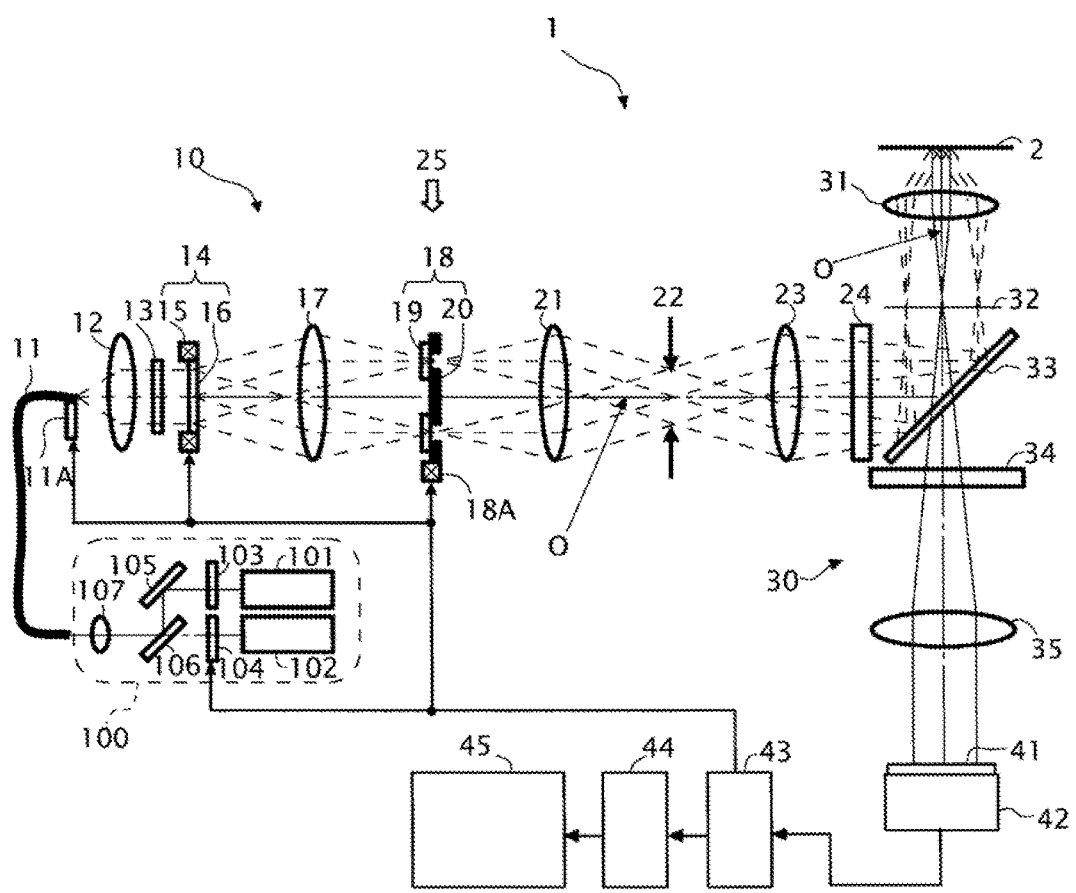
FIG. 1 illustrates the configuration of a structured illumination microscope device 1 according to Embodiment 1.

FIG. 1 illustrates the configuration of a structured illumination microscope device 1. In the following description, the structured illumination microscope device 1 is used as a total internal reflection fluorescence microscope (TIRFM) as an example—in other words, the structured illumination microscope device 1 is used in a TIRFM-SIM mode. TIRFM-SIM mode refers to a mode in which an extremely thin layer of the surface of a sample (specimen) 2 that exhibits fluorescence is observed.

First, the configuration of the structured illumination microscope device 1 will be described.

As illustrated in FIG. 1, the structured illumination microscope device 1 includes a laser unit 100, an optical fiber 11, an illumination optical system 10, an imaging optical system 30, an image sensor 42, a control device 43, an image storage/processing device 44, and an image display device 45. The illumination optical system 10 is an epi-illumination optical system and illuminates the sample 2 using an objective lens 31 and a dichroic mirror 33 of the imaging optical system 30.

The laser unit 100 includes a first laser light source 101, a second laser light source 102, shutters 103 and 104, a mirror 105, a dichroic mirror 106, and a lens 107. The first laser light source 101 and the second laser light source 102 are both coherent light sources and emit different wavelengths of light. Here, assume that the wavelength λ1 of the first laser light source 101 is greater than the wavelength λ2 of the second laser light source 102 (that is, λ1>λ2). The first laser light source 101, the second laser light source 102, and the shutters 103 and 104 are driven by the control device 43.

The optical fiber 11 is a polarization-maintaining single-mode fiber, for example, and guides laser light emitted from the laser unit 100. The position of the output end of the optical fiber 11 can be adjusted in the optical axis O direction by a position adjusting mechanism 11A. The position adjusting mechanism 11A is driven and controlled by the control device 43. The position adjusting mechanism 11A may be a piezo element or the like, for example.

Furthermore, when a polarization-maintaining single-mode fiber is used for the optical fiber 11, the polarization plane of the laser light is maintained while traveling through the optical fiber 11, and therefore a polarizing plate 13 is not strictly required. However, including the polarizing plate 13 is effective in maintaining the quality of the polarized light in the laser light. In contrast, if a multi-mode fiber is used for the optical fiber 11, the polarizing plate 13 is always necessary.

The illumination optical system 10 includes, in order from the output end of the optical fiber 11, a collector lens 12, the polarizing plate 13, a light beam splitter 14, a condenser lens 17, a light beam selector 18, a lens 21, a field diaphragm 22, a field lens 23, an excitation filter 24, the dichroic mirror 33, and the objective lens 31.

The light beam splitter 14 includes a translation mechanism 15 and a diffractive optical element (a diffraction grating) 16. The light beam selector 18 includes a half-wave plate 19, a beam selection member 20, and a rotation mechanism 18A. The light beam splitter 14 and the light beam selector 18 are driven by the control device 43.

The imaging optical system 30 includes, in order from the sample 2, the objective lens 31, the dichroic mirror 33, an absorption filter 34, and a second objective lens 35.

The sample 2 is fluorescent cells (that is, cells stained using a fluorescent dye) arranged on a plane-parallel plate-shaped glass surface or fluorescent living cells (that is, moving cells stained with a fluorescent dye) grown in a petri dish, for example. Each of these cells has both a first fluorescent region that is excited by the light of wavelength $\lambda 1$ and a second fluorescent region that is excited by the light of wavelength $\lambda 2$.

When the structured illumination microscope device 1 is used in the TIRFM-SIM mode, the objective lens 31 functions as a liquid immersion objective (such as an oil immersion objective) in order to make it possible to observe the sample using entirely reflected fluorescent light. In other words, an immersion liquid (oil) is filled into the gap between the objective lens 31 and the glass on which the sample 2 is arranged.

The image sensor 42 is a two-dimensional image sensor such as a CCD or a CMOS sensor. The image sensor 42 is driven by the control device 43 and captures the image formed on the imaging surface 41 in order to generate an image. This image is then sent to the control device 43 and stored in the image storage/processing device 44. The frame period of the image sensor 42 (that is, the period at which imaging is repeated) is determined by the limiting factor among factors such as the imaging time of the image sensor 42 (that is, the time needed to store electric charges and read out those electric charges), the time needed to switch the direction of the interference fringes, and other required times.

The control device 43 controls the laser unit 100, the position adjusting mechanism 11A, the light beam splitter 14, the light beam selector 18, and the image sensor 42.

The image storage/processing device 44 processes the image sent via the control device 43, stores the processed image in an internal memory device (not illustrated in the figure), and outputs the processed image to the image display device 45.

Next, the behavior of the laser light in the structured illumination microscope device 1 will be described.

The laser light of wavelength $\lambda 1$ (first laser light) emitted from the first laser light source 101 travels past the shutter 103 to the mirror 105, reflects off of the mirror 105, and continues to the dichroic mirror 106. Meanwhile, the laser light of wavelength $\lambda 2$ (second laser light) emitted from the second laser light source 102 travels past the shutter 104 to the dichroic mirror 106 and is combined with the first laser light. The first laser light and the second laser light emitted from the dichroic mirror 106 pass through the lens 107 and enter the input end of the optical fiber 11. Moreover, the control device 43 controls the laser unit 100 to switch the wavelength of the laser light that enters the input end of the optical fiber 11 (that is, the wavelength used $\lambda$) between the longer wavelength $\lambda 1$ and the shorter wavelength $\lambda 2$.

The laser light that enters the input end of the optical fiber 11 propagates through the optical fiber 11 and creates a point light source at the output end of the optical fiber 11. The laser light emitted from that point light source is converted to a parallel beam by the collector lens 12 and then travels through the polarizing plate 13 to the diffraction grating 16 of the light beam splitter 14, where the laser light is split into diffracted beams of various orders. These diffracted beams of various orders (hereinafter, "diffracted beam group") are focused by the condenser lens 17 on different positions on a pupil conjugate plane 25.

Here, the pupil conjugate plane 25 is positioned at the focal point of the lens 17 (the focal point on the downstream side) and is said to have a position conjugate to the pupil 32 of the objective lens 31 (at the positions at which the ±first-order diffracted light is focused) via the lens 23 and the lens 21. The lens 17 is arranged such that the focal point of the lens 17 (the focal point on the downstream side) falls on the pupil conjugate plane 25. These conjugate positions are determined according to factors such as the aberration and vignetting of the lenses 17, 21, and 23 that must be considered by one of ordinary skill in the art during design.

The laser light emitted from the optical fiber 11 is typically linearly polarized light, and therefore the polarizing plate 13 can be removed. However, including the polarizing plate 13 is effective in reliably cutting out unneeded polarization components. Furthermore, it is preferable that the axis of the polarizing plate 13 be aligned with the polarization direction of the laser light emitted from the optical fiber 11 in order to increase the laser light utilization efficiency.

Next, the diffracted beams of each order traveling towards the pupil conjugate plane 25 enter the light beam selector 18 arranged near the pupil conjugate plane 25.

When the structured illumination microscope device 1 according to the present embodiment is used in the TIRFM-SIM mode, the light beam selector 18 selectively transmits only one pair of diffracted beams (here, the ±first-order diffracted beams) of the diffracted beams of each order incident on the light beam selector 18.

The ±first-order diffracted beams that pass through the light beam selector 18 are concentrated by the lens 21 on a plane near the field diaphragm 22 that is conjugate to the diffraction grating 16. Then, the ±first-order diffracted beams are converted to focused light by the field lens 23, pass through the excitation filter 24, reflect off of the dichroic mirror 33, and are focused at different positions on the pupil plane 32 of the objective lens 31.

The ±first-order diffracted beams that are concentrated on the pupil plane 32 are emitted from the end of the objective lens 31 as parallel beams and interfere with one another on the surface of the sample 2, forming interference fringes. These interference fringes are used as structured illumination light.

Furthermore, when the structured illumination microscope device 1 according to the present embodiment is used in the TIRFM-SIM mode, the angle of incidence of the light incident on the surface of the sample 2 satisfies a condition that results in creation of an evanescent field. This condition is known as the total internal reflection condition (TIRF condition) or the like. In order to satisfy this TIRF condition, the focused light spots formed by the ±first-order diffracted beams on the pupil plane 32 must fall within a prescribed circular band-shaped region (a TIRF region) positioned on the outermost periphery of the pupil plane 32 (this will be described in more detail later). When this condition is satisfied, the structured illumination light creates an evanescent field near the surface of the sample 2.

When the sample 2 is illuminated with this structured illumination light, the difference between the periodic structure of the structured illumination light and the periodic structure of the fluorescent regions of the sample 2 produces a moire fringe. In this moire fringe, the high frequency structures of the sample 2 are shifted to frequencies lower than the original frequencies, and the light (fluorescent light) produced by these structures returns towards the objective lens 31 at angles smaller than the original angles. As a result, when the sample 2 is illuminated with the structured illumination light, even the high frequency structural information of the fluorescent regions of the sample 2 is transmitted by the objective lens 31.

The fluorescent light produced by the sample 2 enters the objective lens 31 and is converted to parallel light by the objective lens 31. This light then proceeds through the dichroic mirror 33, the barrier filter 34, and the second objective lens 35 and forms a modulated image of the sample 2 on the imaging surface 41 of the image sensor 42.

This modulated image is translated into an image by the image sensor 42 and then sent to the control device 43 and stored in the image storage/processing device 44. Furthermore, the image storage/processing device 44 applies a well-known demodulation process (described in more detail later) to the modulated images stored therein to generate a demodulated image (a super-resolution image). Furthermore, this super-resolution image is stored in the internal memory device (not illustrated in the figure) of the image storage/processing device 44 and then sent to the image display device 45. One example of a well-known demodulation process is the method disclosed in U.S. Pat. No. 8,115,806. This method will be described in more detail later.

Next, the light beam splitter 14 will be described in detail.

Figure 2A:
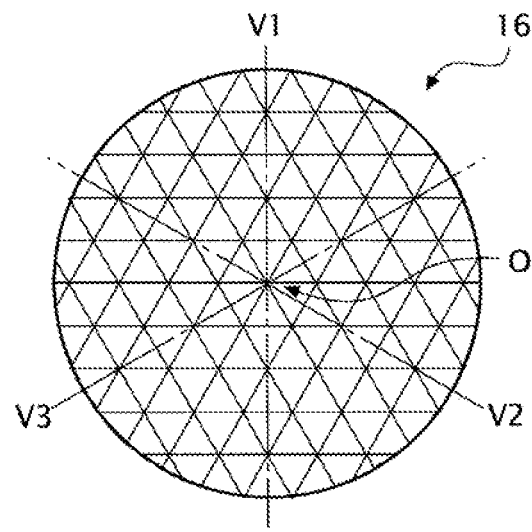
FIGS. 2A and 2B illustrate a light beam splitter 14.
Figure 2B:
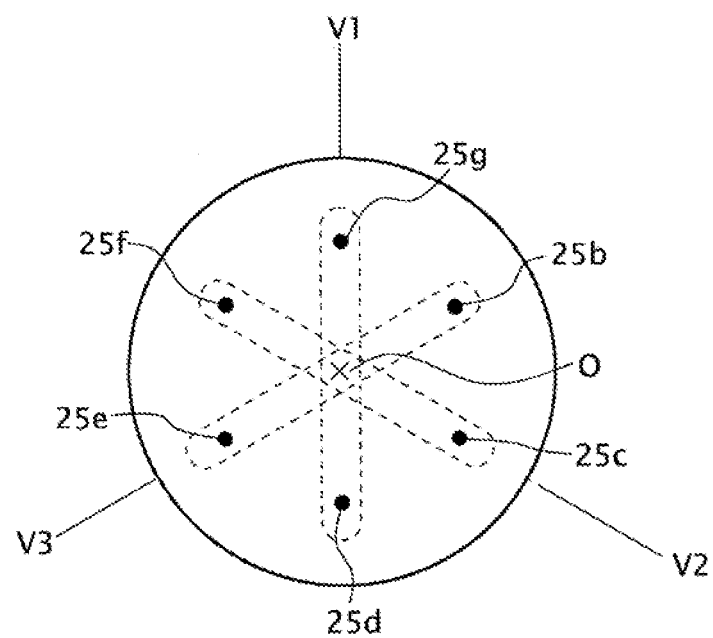

FIGS. 2A and 2B illustrate the light beam splitter 14. FIG. 2A illustrates the diffraction grating 16 of the light beam splitter 14 as viewed from the optical axis O direction, and FIG. 2B illustrates the positional relationship of the focused light spots formed on the pupil conjugate plane by the ±first-order diffracted beams. Note that FIG. 2A is only a schematic drawing, and the actual periodic structure used for the diffraction grating 16 is not limited to the periodic structure illustrated in FIG. 2A.

As illustrated in FIG. 2A, the diffraction grating 16 has a periodic structure that extends in a plurality of different directions in a plane orthogonal to the optical axis O of the illumination optical system 10. The diffraction grating 16 is made from a fused quartz material, for example. Here, the diffraction grating 16 has a periodic structure that extends in a first direction V1, a second direction V2, and a third direction V3 each rotated about the optical axis O by 120° relative to one another. It is assumed that the periodic structure of the diffraction grating 16 is the same in all three directions.

The periodic structure of the diffraction grating 16 may be a concentration-type periodic structure formed by taking advantage of concentration (transmittance) or a phase difference-type periodic structure formed by taking advantage of level differences (phase differences). However, it is preferable that the periodic structure be a phase difference type periodic structure because this type of periodic structure exhibits higher diffraction efficiency of the ±first-order diffracted light.

The parallel beam that enters the diffraction grating 16 is converted into a first diffracted beam group split in the first direction V1, a second diffracted beam group split in the second direction V2, and a third diffracted beam group split in the third direction V3.

The first diffracted beam group contains a zero-order diffracted beam and ±first-order diffracted beams. Of these diffracted beams, the diffracted beams of the same order (that is, the ±first-order diffracted beams) proceed in directions symmetric about the optical axis O.

Similarly, the second diffracted beam group contains a zero-order diffracted beam and ±first-order diffracted beams. Of these diffracted beams, the diffracted beams of the same order (that is, the ±first-order diffracted beams) proceed in directions symmetric about the optical axis O.

Likewise, the third diffracted beam group contains a zero-order diffracted beam and ±first-order diffracted beams. Of these diffracted beams, the diffracted beams of the same order (that is, the ±first-order diffracted beams) proceed in directions symmetric about the optical axis O.

The ±first-order diffracted beams of the first diffracted beam group, the ±first-order diffracted beams of the second diffracted beam group, and the ±first-order diffracted beams of the third diffracted beam group are focused at different positions on the pupil conjugate plane by the condenser lens 17.

Furthermore, as illustrated in FIG. 2B, the focused light spots 25$d$ and 25$g$ formed by the ±first-order diffracted beams of the first diffracted beam group are symmetric about the optical axis O, and the direction in which the focused light spots 25$d$ and 25$g$ are arranged corresponds to the first direction V1.

Here, the distance D from the optical axis O to the focused light spots 25$d$ and 25$g$ is given by the following formula, where $\lambda$ is the wavelength of the laser light emitted from the optical fiber 11, P is the pitch of the periodic structure of the diffraction grating 16, and fc is the focal length of the lens 17.

$$D \propto fc\lambda/P$$

Therefore, changing the wavelength $\lambda$ of the laser light shifts the positions of the focused light spots 25$d$ and 25$g$.

Moreover, the focused light spots 25$c$ and 25$f$ formed by the ±first-order diffracted beams of the second diffracted beam group are symmetric about the optical axis O, and the direction in which the focused light spots 25$c$ and 25$f$ are arranged corresponds to the second direction V2. Note that for the same wavelength $\lambda$, the distance from the optical axis O to the focused light spots 25$c$ and 25$f$ formed by the second diffracted beam group is the same as the distance from the optical axis O to the focused light spots 25$d$ and 25$g$ formed by the first diffracted beam group.

Furthermore, the focused light spots 25$b$ and 25$e$ formed by the ±first-order diffracted beams of the third diffracted beam group are symmetric about the optical axis O, and the direction in which the focused light spots 25$b$ and 25$e$ are arranged corresponds to the third direction V3. Note that for the same wavelength $\lambda$, the distance from the optical axis O to the focused light spots 25$b$ and 25$e$ formed by the third diffracted beam group is the same as the distance from the optical axis O to the focused light spots 25$d$ and 25$g$ formed by the first diffracted beam group.

Here, the term "focused light spots" refers to the weighted center positions of regions that have an intensity of at least 80% of the maximum intensity. Therefore, in the illumination optical system 10 of the present embodiment, the light beams do not necessarily have to be focused to the point of forming perfect focused light spots.

In the light beam splitter 14 described above, the translation mechanism 15 is a piezo motor or the like. The translation mechanism 15 moves the diffraction grating 16 in a direction that is orthogonal to the optical axis O of the illumination optical system 10 but not orthogonal to the first direction V1, the second direction V2, or the third direction V3. Moving the diffraction grating 16 in this direction shifts the phase of the fringes in the structured illumination light (this will be described in more detail later).

Next, the light beam selector 18 will be described in detail.

Figure 3A:
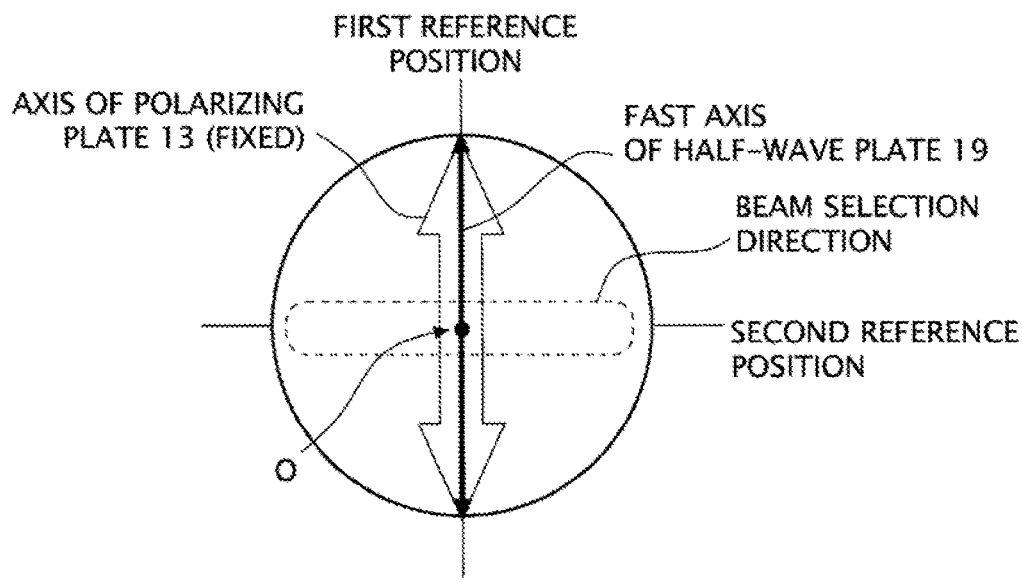
FIGS. 3A and 3B illustrate the function of a half-wave plate 19 of a light beam selector 18.
Figure 3B:
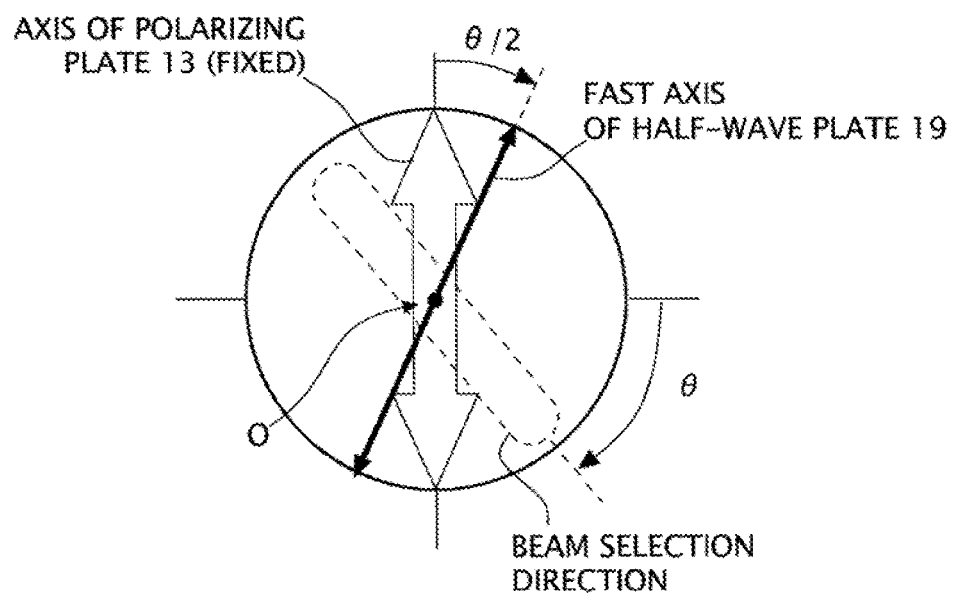
Figure 4A:
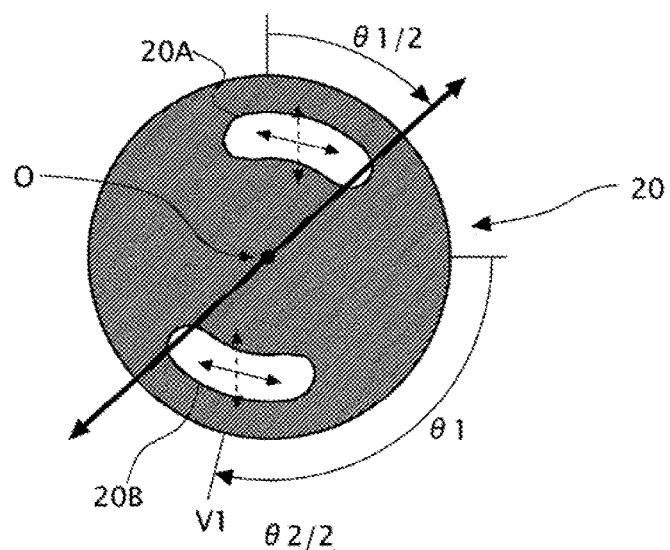
FIGS. 4A to 4C illustrate the function of a beam selection member 20 of the light beam selector 18.
Figure 4B:
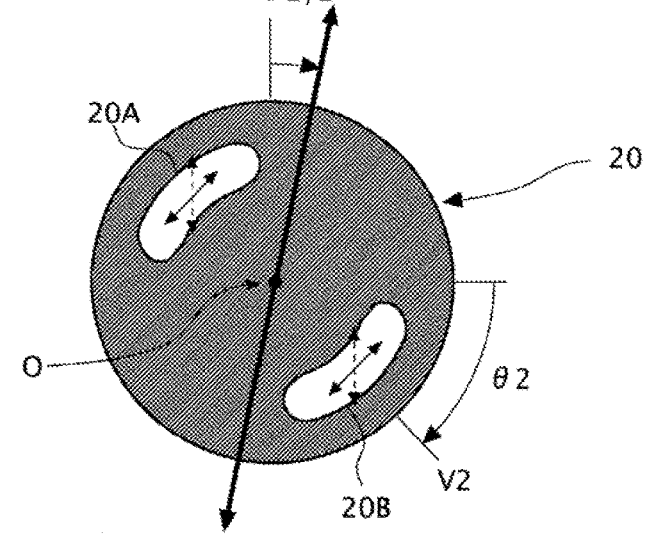
Figure 4C:
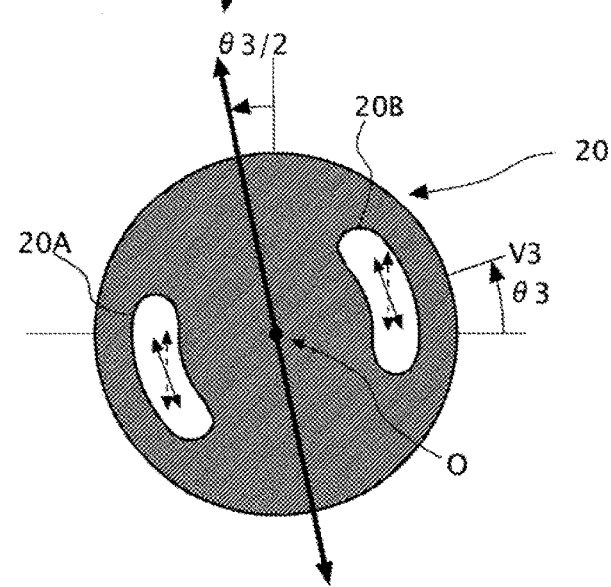

FIGS. 3A to 4C illustrate the light beam selector 18. As illustrated in FIGS. 3A and 3B, the half-wave plate 19 of the light beam selector 18 sets the polarization direction of the diffracted beams of each order incident thereon. As illustrated in FIGS. 4A to 4C, the beam selection member 20 of the light beam selector 18 is a mask that selectively transmits just the ±first-order diffracted beams of one of the diffracted beam groups among the first to third diffracted beam groups.

The rotation mechanism 18A of the light beam selector 18 rotates the beam selection member 20 about the optical axis O in order to switch the selected ±first-order diffracted beams of the first to third diffracted beam groups. The rotation mechanism 18A also rotates the half-wave plate 19 about the optical axis O in unison with the beam selection member 20 in order to keep the selected ±first-order diffracted beams that are incident on the sample 2 s-polarized.

In other words, the light beam selector 18 switches the direction of the structured illumination light fringes while maintaining the state of those structured illumination light fringes.

The rotation mechanism 18A includes, for example, a support member (not illustrated in the figures) that supports the beam selection member 20 and allows the beam selection member 20 to rotate about the optical axis O, a first gear (not illustrated in the figures) formed surrounding the support member, a second gear (not illustrated in the figures) that meshes with the first gear, and a motor (a rotation motor-not illustrated in the figures) that is connected to the second gear. Activating this motor rotates the second gear, and this rotary force is transmitted to the first gear, thereby rotating the beam selection member 20 about the optical axis O.

Next, the conditions for maintaining the state of the fringes will be described in more detail.

First, the fast axis of the half-wave plate 19 must be oriented such that the polarization direction of the selected ±first-order diffracted beams is orthogonal to the direction in which the selected ±first-order diffracted beams are split (one of the first direction V1 to third direction V3). Here, the "fast axis" of the half-wave plate 19 refers to the axis in the direction in which the phase delay of light polarized in that direction by passing through the half-wave plate 19 is minimized.

An opening pattern formed in the beam selection member 20 includes a first opening 20A and a second opening 20B that each allow one of the ±first-order diffracted beams of the same diffracted beam group to pass through. The lengths of the first opening 20A and the second opening 20B around the optical axis O are set to lengths that allow the linearly polarized diffracted beams that are polarized in the above-mentioned direction to pass through. Therefore, the first opening 20A and the second opening 20B both have a partial ring shape.

Here, the rotation position of the half-wave plate 19 illustrated in FIG. 3A, in which the fast axis of the half-wave plate 19 is parallel to the axis of the polarizing plate 13, serves as a reference rotation position for the half-wave plate 19 (hereinafter, a "first reference position").

Furthermore, the rotation position of the beam selection member 20 in which the beam selection direction of the beam selection member 20 (that is, the direction in which the selected ±first-order diffracted beams are split) is orthogonal to the axis of the polarizing plate 13 serves as a reference rotation position for the beam selection member 20 (hereinafter, a "second reference position").

As illustrated in FIG. 3B, the rotation of the half-wave plate 19 and the beam selection member 20 should be controlled such that the amount by which the half-wave plate 19 is rotated from the first reference position is equal to half of the amount by which the beam selection member 20 is rotated from the second reference position.

In other words, when the half-wave plate 19 is rotated by $\theta/2$ from the first reference position, the beam selection member 20 is rotated by $\theta$ from the second reference position.

Therefore, as illustrated in FIG. 4A, in order to select the ±first-order diffracted beams of the first diffracted beam group (that are split in the first direction V1), the rotation mechanism 18A of the light beam selector 18 rotates the beam selection member 20 clockwise such that the beam selection direction thereof is rotated by an angle of $\theta 1$ from the second reference position and also rotates the half-wave plate 19 clockwise such that the fast axis thereof is rotated by an angle of $\theta 1/2$ from the first reference position.

As illustrated by the dashed arrows in FIG. 4A, the polarization direction of the diffracted beams of each order before passing through the half-wave plate 19 are parallel to the axis of the polarizing plate 13. However, as illustrated by the solid arrows in FIG. 4A, the polarization direction of the diffracted beams of each order after passing through the half-wave plate 19 is rotated clockwise by an angle of $\theta 1$, and therefore the polarization direction of the selected ±first-order diffracted beams is orthogonal to the direction in which those ±first-order diffracted beams were split (the first direction V1).

In other words, the direction of the fast axis of the half-wave plate 19 is set according to the direction in which the ±first-order diffracted beams selected by the beam selection member 20 are split (the first direction V1) such that the fast axis of the half-wave plate 19 bisects the angle between the polarization direction of the ±first-order diffracted beams incident on the half-wave plate 19 (that is, the direction of the axis of the polarizing plate 13) and the polarization direction that the ±first-order diffracted beams should have after exiting from the half-wave plate 19 (that is, the direction orthogonal to the first direction V1).

Moreover, as illustrated in FIG. 4B, in order to select the ±first-order diffracted beams of the second diffracted beam group (that are split in the second direction V2), the rotation mechanism 18A of the light beam selector 18 rotates the beam selection member 20 clockwise such that the beam selection direction thereof is rotated by an angle of $\theta 2$ from the second reference position and also rotates the half-wave plate 19 clockwise such that the fast axis thereof is rotated by an angle of $\theta 2/2$ from the first reference position.

As illustrated by the dashed arrows in FIG. 4B, the polarization direction of the diffracted beams of each order before passing through the half-wave plate 19 are parallel to the axis of the polarizing plate 13. However, as illustrated by the solid arrows in FIG. 4B, the polarization direction of the diffracted beams of each order after passing through the half-wave plate 19 is rotated clockwise by an angle of θ2, and therefore the polarization direction of the selected ±first-order diffracted beams is orthogonal to the direction in which those ±first-order diffracted beams were split (the second direction V2).

In other words, the direction of the fast axis of the half-wave plate 19 is set according to the direction in which the ±first-order diffracted beams selected by the beam selection member 20 are split (the second direction V2) such that the fast axis of the half-wave plate 19 bisects the angle between the polarization direction of the ±first-order diffracted beams incident on the half-wave plate 19 (that is, the direction of the axis of the polarizing plate 13) and the polarization direction that the ±first-order diffracted beams should have after exiting from the half-wave plate 19 (that is, the direction orthogonal to the second direction V2).

Similarly, as illustrated in FIG. 4C, in order to select the ±first-order diffracted beams of the third diffracted beam group (that are split in the third direction V3), the rotation mechanism 18A of the light beam selector 18 rotates the beam selection member 20 counter-clockwise (as viewed from the sample side—the same applies below) such that the beam selection direction thereof is rotated by an angle of θ3 from the second reference position and also rotates the half-wave plate 19 counter-clockwise such that the fast axis thereof is rotated by an angle of θ3/2 from the first reference position.

As illustrated by the dashed arrows in FIG. 4C, the polarization direction of the diffracted beams of each order before passing through the half-wave plate 19 are parallel to the axis of the polarizing plate 13. However, as illustrated by the solid arrows in FIG. 4C, the polarization direction of the diffracted beams of each order after passing through the half-wave plate 19 is rotated counter-clockwise by an angle of θ3, and therefore the polarization direction of the selected ±first-order diffracted beams is orthogonal to the direction in which those ±first-order diffracted beams were split (the third direction V3).

In other words, the direction of the fast axis of the half-wave plate 19 is set according to the direction in which the ±first-order diffracted beams selected by the beam selection member 20 are split (the third direction V3) such that the fast axis of the half-wave plate 19 bisects the angle between the polarization direction of the ±first-order diffracted beams incident on the half-wave plate 19 (that is, the direction of the axis of the polarizing plate 13) and the polarization direction that the ±first-order diffracted beams should have after exiting from the half-wave plate 19 (that is, the direction orthogonal to the third direction V3).

Therefore, the rotation mechanism 18A of the light beam selector 18 should rotate the half-wave plate 19 and the beam selection member 20 at a gear ratio of 2:1.

In the description above, the rotatable half-wave plate 19 is used to maintain the s-polarization of the ±first-order diffracted beams incident on the sample 2. However, the rotatable half-wave plate 19 may be replaced by a fixed liquid crystal element that is used to achieve the same effect as the half-wave plate 19. Electronically controlling the orientation of the liquid crystal molecules in the liquid crystal element makes it possible to control the anisotropicity of the refractive index of the liquid crystal element, thereby making it possible to effectively rotate the fast axis of the half-wave plate about the optical axis O. There are also other ways of maintaining the s-polarization of the ±first-order diffracted beams incident on the sample 2 (these will be described later).

Figure 5:
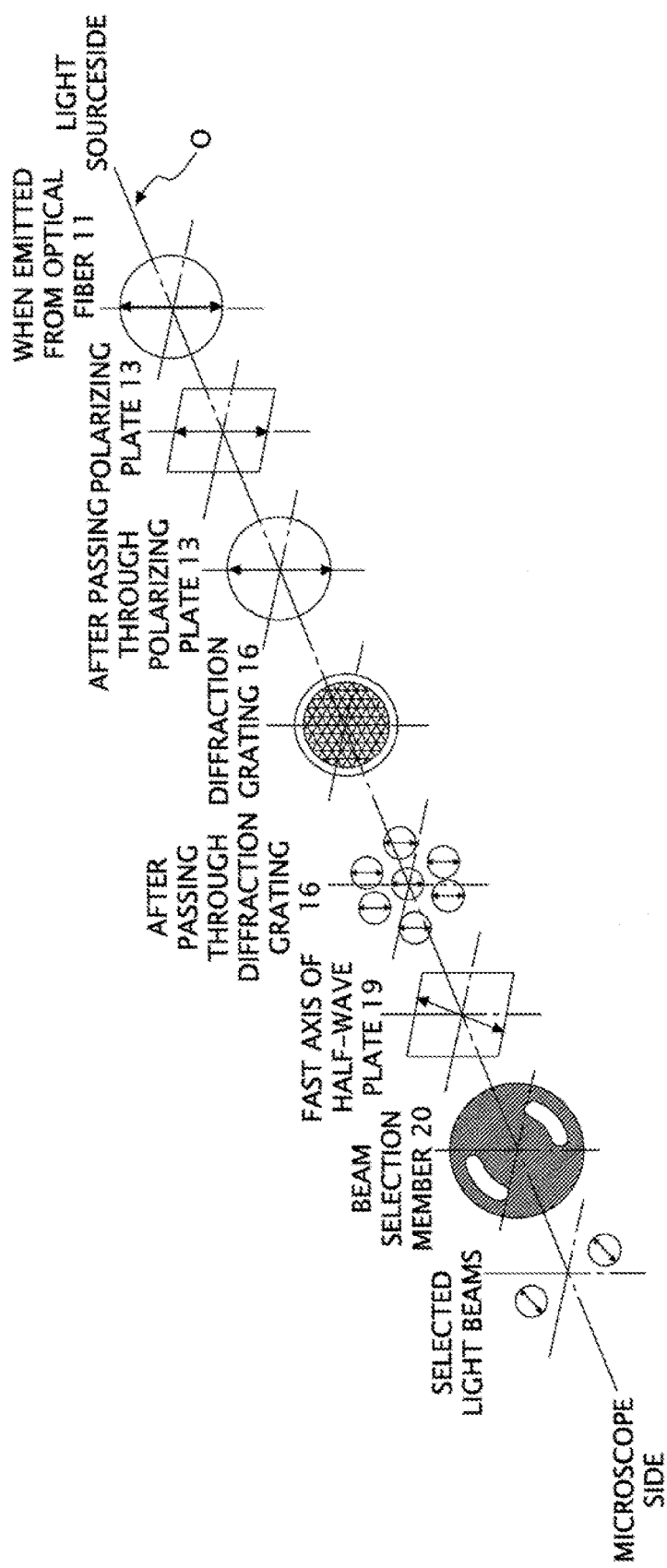
FIG. 5 illustrates the function of the light beam selector 18.

FIG. 5 illustrates the function of the light beam selector 18 as described above. In FIG. 5, the arrows surrounded by circles indicate the polarization direction of the light beams, and the arrows surrounded by squares indicate the direction in which the axis of an optical element is oriented.

Figure 6:
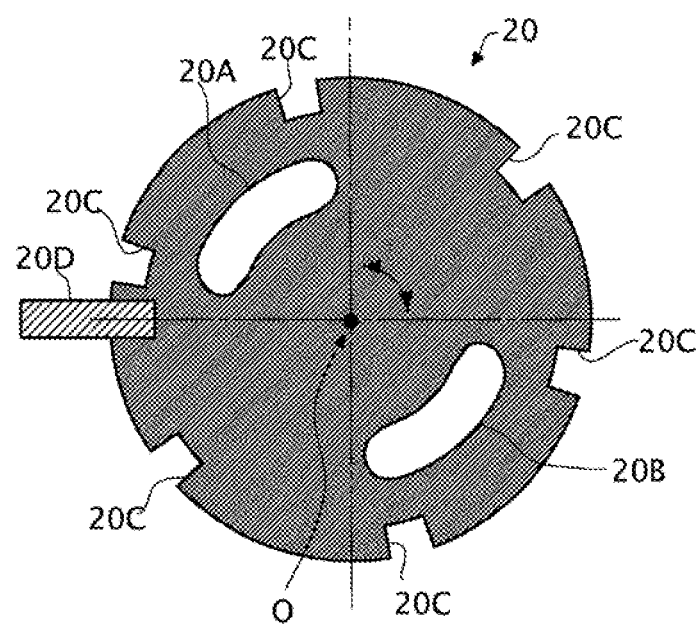
FIG. 6 illustrates a rotation mechanism 18A of the light beam selector 18.

Moreover, as illustrated in FIG. 6, a plurality of slits 20C (six slits in the example illustrated in FIG. 6) are formed in the periphery of the beam selection member 20, and the rotation mechanism 18A includes a timing sensor 20D for detecting the slits 20C. This makes it possible for the rotation mechanism 18A to detect not only the rotation angle of the light beam selector 18 but also the rotation angle of the half-wave plate 19.

Next, the translation mechanism 15 of the light beam splitter 14 will be described in detail.

FIG. 7 illustrates the operation of the translation mechanism 15 of the light beam splitter 14.

In order to be able to apply the demodulation process described above, at least three modulated images of the same sample 2 in which the direction of the interference fringes is the same but the phases of the interference fringes are different are required. This is because the modulated images of the structures of the sample 2 that are generated by the structured illumination microscope device 1 contain a zero-order modulation component, a ±first-order modulation component, and a −first-order modulation component, which represent structural information in which the spatial frequency is modulated due to the structured illumination light. In order to make these three unknown parameters known during the demodulation process (described in more detail later), the number of modulated images must be greater than or equal to the number of unknown parameters.

Figure 7A:
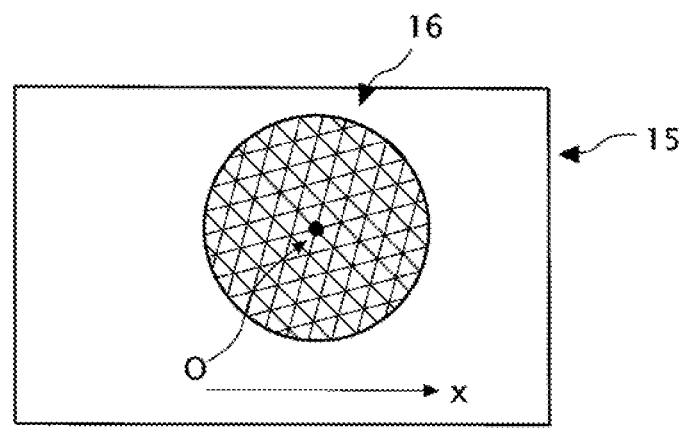
FIGS. 7A and 7B illustrate the operation of a translation mechanism 15 of the light beam splitter 14.

Therefore, as illustrated in FIG. 7A, the translation mechanism 15 of the light beam splitter 14 shifts the diffraction grating 16 in a direction (the x direction) that is orthogonal to the optical axis O of the Illumination optical system 10 but not orthogonal to any of the first direction V1, the second direction V2, or the third direction V3 in order to shift the phase of the interference fringes.

However, the distance L by which the diffraction grating 16 must be shifted in order to shift the phase of the interference fringes by a desired amount 4 is not necessarily the same when the beam selection direction of the light beam selector 18 is the first direction V1, when the beam selection direction is the second direction V2, and when the beam selection direction is the third direction V3.

Figure 7B:
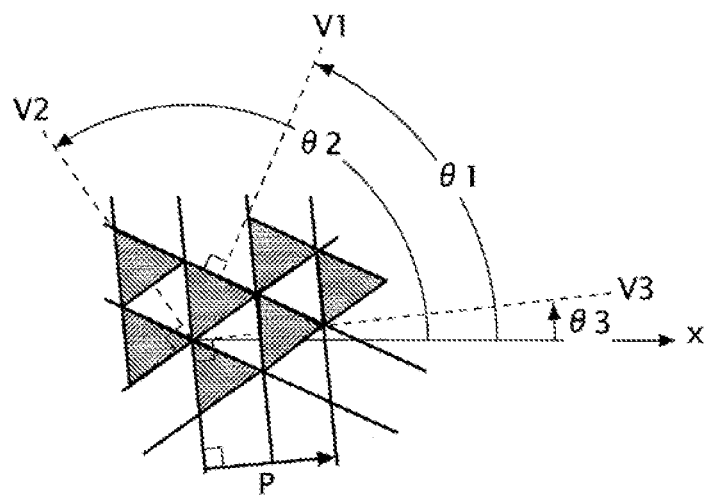

As illustrated in FIG. 7B, let P be the pitch of the periodic structures of the diffraction grating 16 in the first direction V1, the second direction V2, and the third direction V3. Let θ1 be the angle between the direction in which the diffraction grating 16 is shifted (the x direction) and the first direction V1, let θ2 be the angle between the direction in which the diffraction grating 16 is shifted (the x direction) and the second direction V2, and let θ3 be the angle between the direction in which the diffraction grating 16 is shifted (the x direction) and the third direction V3. In this case, the distance L1 by which the diffraction grating 16 must be shifted in the x direction when the beam selection direction is the first direction V1 is $L1=\phi \times P/(a \times 4\pi \times |\cos \theta 1|)$, the distance L2 by which the diffraction grating 16 must be shifted in the x direction when the beam selection direction is the second direction V2 is $L2=\phi \times P/(a \times 4\pi \times |\cos \theta 2|)$, and the distance L3 by which the diffraction grating 16 must be shifted in the x direction when the beam selection direction is the third direction V3 is L3=φ×P/(a×4π×|cos θ3|).

In other words, the distance L by which the diffraction grating 16 must be shifted in the x direction to achieve a desired phase shift of φ in the interference fringes depends on the angle θ between the beam selection direction (the first direction V1, the second direction V2, or the third direction V3) and the x direction, as given below by equation (1).

$$L=\phi \times P/(a \times 4\pi \times |\cos \theta|) \quad (1)$$

The distance L by which the diffraction grating 16 must be shifted in the x direction to achieve a phase shift φ of 2π in the interference fringes is P/(a×2×|cos θ|). This distance is equal to half of the pitch of the diffraction grating 16. In other words, shifting the diffraction grating 16 by a distance equal to half of the pitch thereof makes it possible to shift the phase of the structured illumination light by a full period (because the pitch of the interference fringes produced by the ±first-order diffracted light is equal to two times the pitch of the periodic structure of the diffraction grating 16).

Next, a configuration of the present embodiment that satisfies the total internal reflection condition (TIRF condition) will be described in detail.

As described above, in the present embodiment the wavelength used λ can be switched between λ1 and λ2. As illustrated by the dotted and solid lines in FIG. 8A, for example, switching the wavelength used λ changes the diffraction angle of the ±first-order diffracted light produced by the diffraction grating 16. In this case, assuming that there is no aberration in the illumination optical system 10, the distance from the optical axis O to the focused light spots formed by the ±first-order diffracted light on the pupil plane 32 changes between the white and black points in FIG. 8B, for example. Here, switching the wavelength used λ may cause the focused light spots formed by the ±first-order diffracted light to fall outside of the TIRF region.

Therefore, in the present embodiment, a prescribed chromatic aberration of magnification is applied to the lenses 17, 21, and 23 (hereinafter, "the light-collecting optical system") arranged between the diffraction grating 16 and the objective lens 13 of the illumination optical system 10. This chromatic aberration of magnification is set such that the focused light spots formed by the ±first-order diffracted light remain within the TIRF region regardless of the wavelength used λ. Next, the details of this configuration will be described.

FIG. 9 illustrates the configuration of the light-collecting optical system (the lenses 17, 21, and 23).

As illustrated in FIG. 9, each of the lenses 17, 21, and 23 is a cemented lens made by bonding together a convex lens and a concave lens. The overall light-collecting optical system (the lenses 17, 21, and 23) satisfies the following condition regardless of the wavelength used λ.

$$(fo \cdot nw - af\lambda/P) \leq dY(\lambda) \leq (fo \cdot NA - af\lambda/P), \quad (2)$$

where a=1 (for M=1, 2) or a=2 (for M=3)

Here, dY(λ) is the chromatic aberration of magnification in the light-collecting optical system for an image of height 2f·λ₀/P created by light of wavelength λ when the wavelength used λ is set to a reference wavelength λ₀. Furthermore, fo is the focal length of the objective lens 31, f is the focal length of the overall light-collecting optical system (the lenses 17, 21, and 23), P is the pitch of the periodic structure of the diffraction grating 16, NA is the numerical aperture of the objective lens 31, M is the number of directions in which the diffraction grating 16 has a periodic structure, and nw is the refractive index of the sample 2.

In the present embodiment, the sample 2 is cells, and therefore nw is substantially equal to the refractive index of water. Moreover, in the present embodiment the number of directions in which the diffraction grating 16 has a periodic structure is 3, and therefore M=3.

Next, the meaning behind conditional expression (2) will be described.

Figure 10:
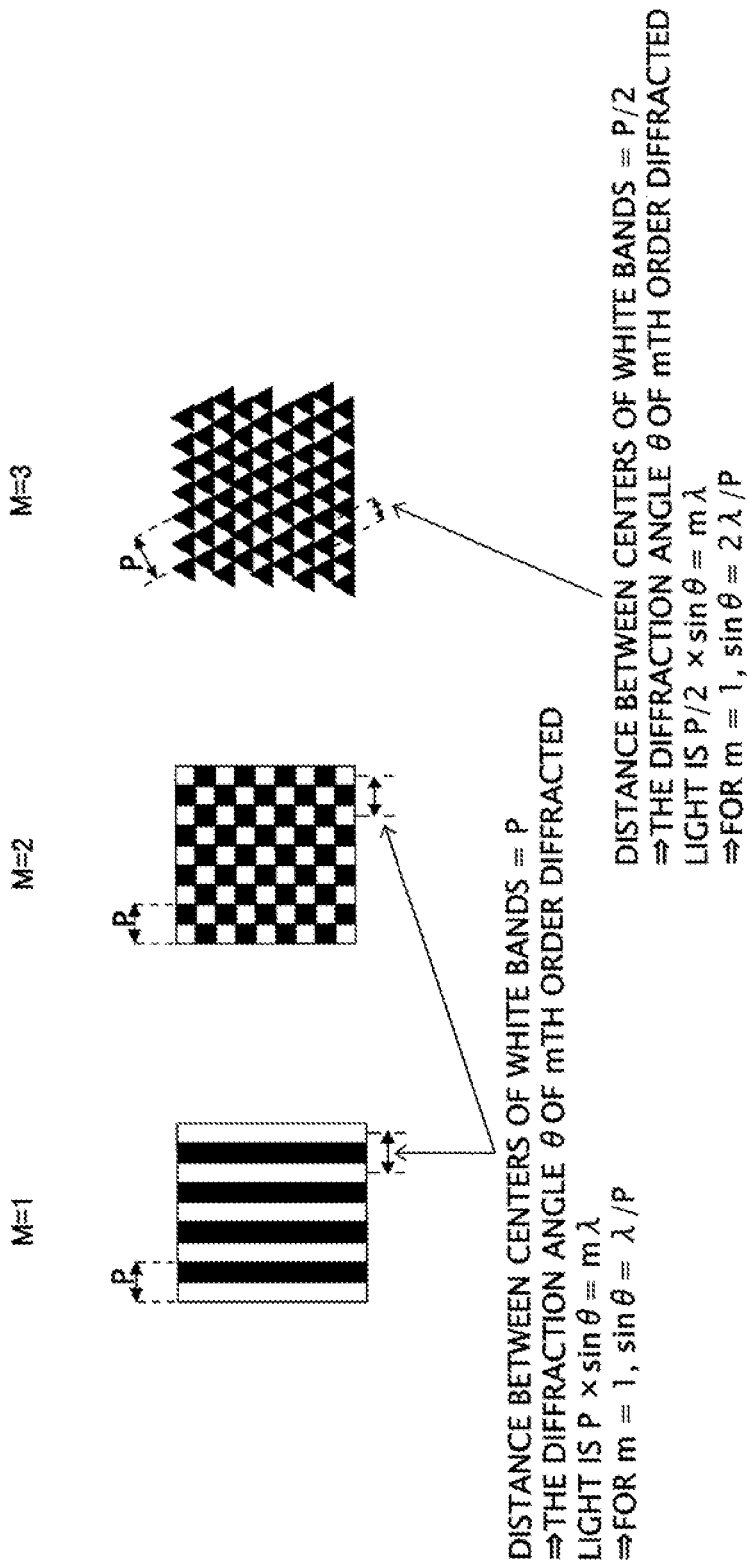
FIG. 10 illustrates the relationship between the number of directions M in which a diffraction grating 16 has a periodic structure and the diffraction angle θ of mth order diffracted light.

First, FIG. 10 illustrates how the diffraction angle θ of the first-order diffracted light produced by the diffraction grating 16 when irradiated with laser light of wavelength λ is related to the pitch P of the periodic structure of the diffraction grating 16 and the number of directions M in which the diffraction grating 16 has a periodic structure. In other words, the diffraction angle θ of the first-order diffracted light is given by following equation.

Here, the angle θ is extremely small, and therefore sin θ≈θ.

$$\theta = a\lambda/P, \quad (3)$$

where a=1 (for M=1, 2) or a=2 (for M=3)

Furthermore, assuming that there is no aberration in the light-collecting optical system (the lenses 17, 21, and 23) and letting f be the focal length of the light-collecting optical system (the lenses 17, 21, and 23), the first-order diffracted light emitted from the diffraction grating 16 at a diffraction angle of θ is focused on the pupil plane 32 at a distance Y from the optical axis O. This distance Y is given by the following equation.

Here, the angle θ is extremely small, and therefore tan θ≈θ.

$$Y = f\theta \quad (4)$$

Moreover, letting fo be the focal length of the objective lens 31 and letting NA be the numerical aperture of the objective lens 31, the radius r of the pupil of the objective lens 31 is given by the following equation.

$$r = foNA \quad (5)$$

Therefore, if the quantity (Y+dY(λ)) satisfies the following conditional expression regardless of the wavelength used λ, then the focused light spots formed by the first-order diffracted light will remain within the TIRF region regardless of the wavelength used λ. In other words, the TIRF condition will remain satisfied.

$$nwfo \leq Y + dY(\lambda) \leq r \quad (6)$$

Substituting equations (3), (4), and (5) into equation (6) and solving the resulting equation for dY yields conditional expression (2).

Therefore, as described above, conditional expression (2) gives the condition that must be satisfied for the focused light spots formed by the ±first-order diffracted light to remain within the TIRF region regardless of the wavelength used λ (that is, to keep the TIRF condition satisfied).

FIG. 11 is a table of lens data for the light-collecting optical system (the lenses 17, 21, and 23) of the present embodiment, and FIG. 12 is a correspondence table of conditions for the light-collecting optical system (the lenses 17, 21, and 23) of the present embodiment.

Note that here, the reference wavelength λ₀ is set to 588 nm. In FIG. 12, the third row from the bottom gives the chromatic aberration of magnification dY(405) for a wavelength of 405 nm, the chromatic aberration of magnification dY(436) for a wavelength of 436 nm, the chromatic aberration of magnification dY(486) for a wavelength of 486 nm, the chromatic aberration of magnification dY(588) for a wavelength of 588 nm, and the chromatic aberration of magnification dY(656) for a wavelength of 656 nm.

As shown in the first and second rows from the bottom in FIG. 12, each of these chromatic aberrations of magnification dY(405), dY(436), dY(486), dY(588), and dY(656) satisfy conditional expression (2).

Therefore, the light-collecting optical system (the lenses 17, 21, and 23) of the present embodiment makes it possible to keep the focused light spots formed by the ±first-order diffracted light within the TIRF region (that is, keep the TIRF condition satisfied) even when the wavelength used λ is switched between 405 nm, 436 nm, 486 nm, 588 nm, and 656 nm.

The distances from the optical axis O to the focused light spots on the pupil plane 32 for each wavelength are as follows.

For a wavelength of 405 nm, the distance is 2.95 mm. For a wavelength of 436 nm, the distance is 2.79 mm. For a wavelength of 486 nm, the distance is 2.70 mm. For a wavelength of 588 nm, the distance is 2.82 mm. For a wavelength of 656 nm, the distance is 2.98 mm.

Therefore, the distance from the optical axis O to the focused light spots remains greater than or equal to a prescribed value (greater than or equal to 2.70 mm) and also remains within a prescribed range (within a range of 2.70 to 2.98 mm) even when the wavelength used λ is switched between 405 nm, 436 nm, 486 nm, 588 nm, and 656 nm (within a wavelength range of ≈400 to ≈700 nm).

In other words, in the present embodiment the chromatic aberration of magnification of the light-collecting optical system is adjusted such that for light in a wavelength range of ≈400 to ≈700 nm, the distance from the optical axis O to the focused light spots remains greater than or equal to a prescribed value (greater than or equal to 2.70 mm), and the change in that distance for different wavelengths remains less than or equal to a prescribed value (less than or equal to ≈0.5 mm).

Therefore, in the structured illumination microscope device 1 according to the present embodiment, the two wavelengths λ1 and λ2 emitted by the laser unit 100 may be set to any two of the wavelengths 405 nm, 436 nm, 486 nm, 588 nm, and 656 nm.

Furthermore, as described above, the light-collecting optical system (the lenses 17, 21, and 23) of the present embodiment has prescribed chromatic aberrations of magnification (the third row from the bottom in FIG. 12) so that the TIRF condition remains satisfied regardless of the wavelength used λ. Meanwhile, as shown in FIG. 13, the axial chromatic aberrations of the light-collecting optical system (the lenses 17, 21, and 23) of the present embodiment stay within a range of −0.119 to +0.586 mm (≈0.8 mm).

Therefore, in the structured illumination microscope device 1 according to the present embodiment, the focus of the light-collecting optical system (the lenses 17, 21, and 23) does not necessarily have to be adjusted when the wavelength used λ is switched.

However, if the axial chromatic aberration of the light-collecting optical system (the lenses 17, 21, and 23) cannot be ignored, the focus may be adjusted when the wavelength used λ is switched.

The focus can be adjusted by adjusting the position of the output end of the optical fiber 11 in the optical axis O direction using the position adjusting mechanism 11A or by adjusting the position of at least one of the lenses 17, 21, and 23 in the optical axis O direction.

Moreover, when adjusting the focus by adjusting the position of one of the lenses in the optical axis O direction, the position of the diffraction grating 16 in the optical axis O direction may also be adjusted as necessary.

In the present embodiment, the laser unit 100 can emit two wavelengths of laser light. However, the number of wavelengths of laser light that can be emitted by the laser unit 100 may also be set to three or more. In this case, the three wavelengths of laser light emitted by the laser unit 100 may be set to any three of the wavelengths 405 nm, 436 nm, 486 nm, 588 nm, and 656 nm.

Furthermore, in the present embodiment the wavelengths of laser light that can be emitted by the laser unit 100 are selected from the wavelengths 405 nm, 436 nm, 486 nm, 588 nm, and 656 nm. However, any wavelengths in the range of 405 to 656 nm may be selected. This is because the light-collecting optical system (the lenses 17, 21, and 23) of the present embodiment satisfies conditional expression (2) for any wavelength in the range of 405 to 656 nm.

Moreover, in the present embodiment the chromatic aberration of magnification of the light-collecting optical system (the lenses 17, 21, and 23) is set such that the focused light spots remain within the TIRF region regardless of the wavelength used λ in order to perform total internal reflection fluorescence (TIRF) microscopy. However, when the TIRF functionality is not needed (that is, when using the structured illumination microscope device 1 in standard SIM mode rather than TIRF-SIM mode), the focused light spots do not have to remain within the TIRF region.

Changing the distance from the optical axis O to the focused light spots by switching the wavelength used λ, however, may also cause changes in the super-resolution effect. Therefore, it is preferable that the chromatic aberration of magnification of the light-collecting optical system (the lenses 17, 21, and 23) be set such that the distance from the optical axis O to the focused light spots is maintained regardless of the wavelength used λ even when TIRF functionality is not needed.

Furthermore, in order to switch the distance from the optical axis O to the focused light spots between a distance suitable for TIRF-SIM mode and a distance suitable for SIM mode, the diffraction grating 16 that is inserted into the light beam path may be switched between a TIRF-SIM mode diffraction grating and a SIM mode diffraction grating. The TIRF-SIM mode diffraction grating and the SIM mode diffraction grating have periodic structures of different periods.

Here, "super-resolution effect SR" refers to a ratio SR=(R+K)/R between the resolution R of the structured illumination microscope device when the sample is not modulated and the resolution (R+K) of the structured illumination microscope device when the sample 2 is modulated.

The non-modulated resolution R is given by $R=2NA/\lambda$, where NA is the numerical aperture of the objective lens and λ is the wavelength used.

Meanwhile, the increase in resolution K when using modulation is equal to the modulation frequency of the sample (that is, the spatial frequency of the interference fringes).

More specifically, K is given by $K=2d/(fo \times \lambda)$, where fo is the focal length of the objective lens.

Therefore, $SR=(R+K)/R=\{(2 \times NA/\lambda)+(2 \times d)/(fo \times \lambda)\}/(2 \times NA/\lambda)$, and; $SR=(fo \times NA+d)/(fo \times NA)$     (10)

Here, because $\theta=(a \times \lambda)/P$ and $d=f \times \theta$, $d=(a \times f \times \lambda)/P$, and equation (10) can be rewritten as:

$SR=\{fo \times NA+(a \times f/P) \times \lambda\}/(fo \times NA)$

This makes it clear that the super-resolution effect SR is dependent on λ. As a result, conventional structured illumination microscope devices suffer from changes in the super-resolution effect SR=(R+K)/R when the wavelength used λ is changed.

In contrast, in the present embodiment the distance from the optical axis O to the focused light spots is maintained regardless of the wavelength used λ (in other words, the variable d in equation (10) is a fixed value that does not depend on λ), and therefore the super-resolution effect (R+K)/R remains constant.

Moreover, in the present embodiment it was assumed that the sample is irradiated with a plurality of different wavelengths of light sequentially (in order to sequentially excite a plurality of types of fluorescent regions). However, the sample may also be irradiated with a plurality of different wavelengths of light simultaneously (in order to simultaneously excite the plurality of types of fluorescent regions). In this case, it is preferable that the structured illumination microscope device 1 include a feature for separating and detecting the plurality of different wavelengths of fluorescent light.

Embodiment 2

Next, a structured illumination microscope device according to Embodiment 2 of the present invention will be described.

The structured illumination microscope device according to the present embodiment is a modification example of the structured illumination microscope device according to Embodiment 1, and therefore only the differences between the present embodiment and Embodiment 1 will be described here.

In Embodiment 1, the structured illumination microscope device 1 is used in a total internal reflection fluorescence structured illumination microscope mode (TIRF-SIM mode). In the present embodiment, however, the structured illumination microscope device 1 can be switched between the total internal reflection fluorescence structured illumination microscope mode (TIRF-SIM mode) and a total internal reflection fluorescence microscope mode that does not use structured illumination (TIRF mode).

In TIRF-SIM mode, although the sample 2 can be observed at a high resolution, several frames of image data must be captured in order to produce a single frame of the super-resolution image. This takes time and can be disadvantageous in some cases. Furthermore, while although setting the number of directions M in which the diffraction grating 16 has a periodic structure to a value greater than or equal to 2 (in order to simultaneously produce a plurality of pairs of diffracted beams) makes it possible to increase the frame rate when capturing a sequence of modulated images, only a single pair of diffracted beams is used for each modulated image, and therefore the utilization efficiency of the laser light is relatively poor.

In TIRF mode, however, although the sample 2 cannot be observed at a high resolution, producing a single frame of the observation image does not require several frames of image data. This takes less time and can be advantageous in some cases. Moreover, the laser light is guided directly to the sample 2 without going through the diffraction grating 16, and therefore the laser light utilization efficiency is relatively high.

Therefore, equipping the structured illumination microscope device 1 with both a TIRF-SIM mode and a TIRF mode can be extremely advantageous.

Figure 14:
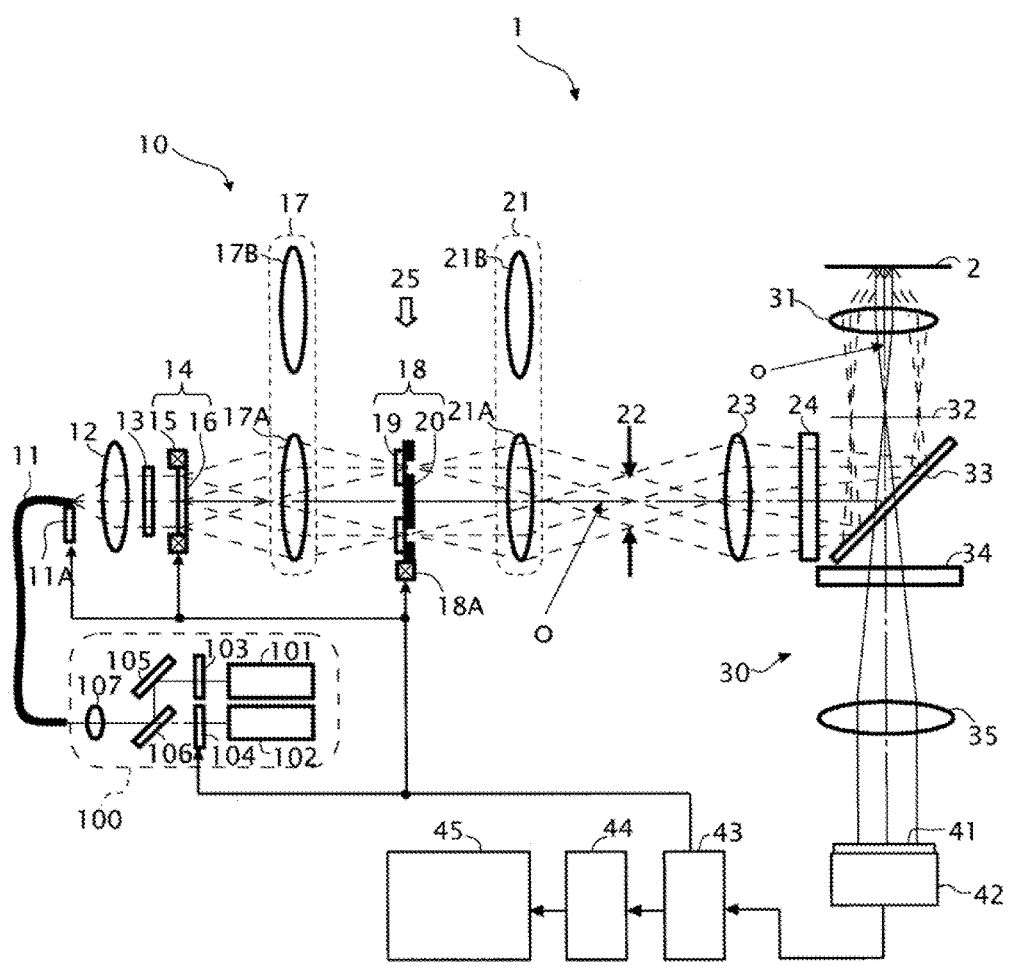
FIG. 14 illustrates the configuration of a structured illumination microscope device 1 according to Embodiment 2 when used in TIRF-SIM mode.
Figure 15:
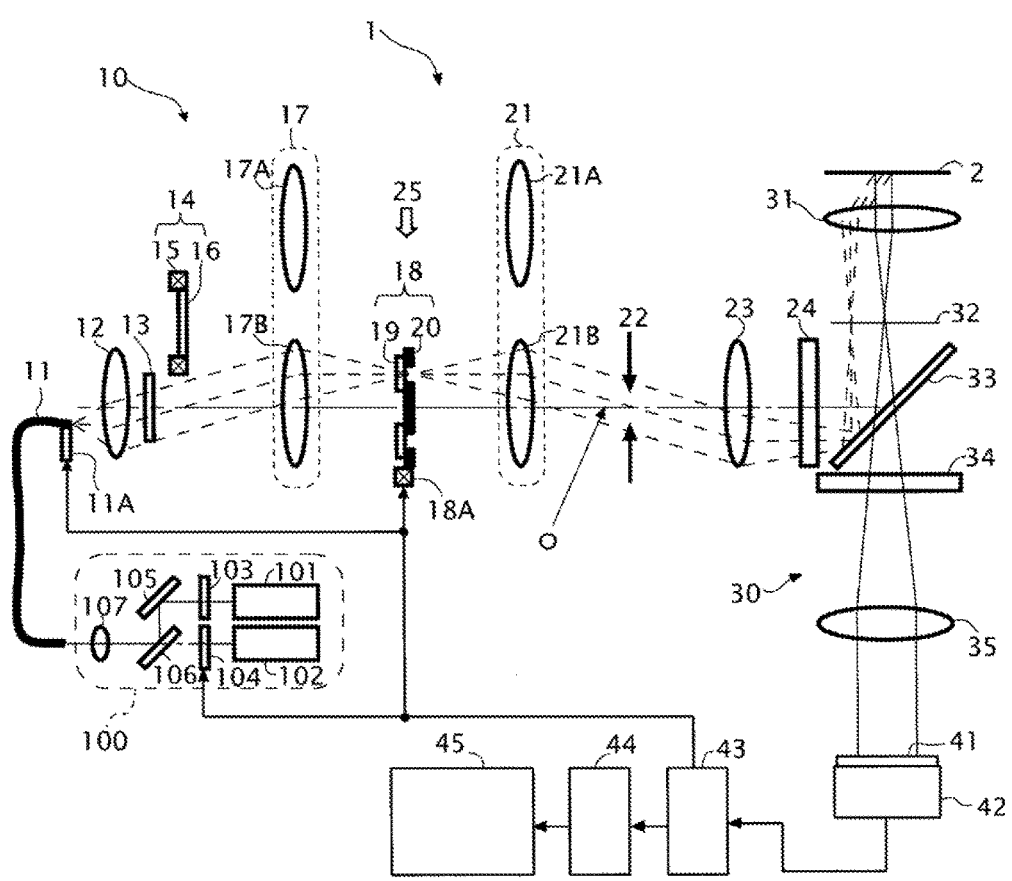
FIG. 15 illustrates the configuration of a structured illumination microscope device 1 according to Embodiment 2 when used in TIRF mode.

FIGS. 14 and 15 illustrate the configuration of the structured illumination microscope device 1 according to the present embodiment. FIG. 14 illustrates the structured illumination microscope device 1 in TIRF-SIM mode, and FIG. 15 illustrates the structured illumination microscope device 1 in TIRF mode.

As illustrated in FIGS. 14 and 15, in the structured illumination microscope device 1 according to the present embodiment, the light beam splitter 14 (the diffraction grating 16) can be inserted into and removed from the light beam path of the illumination optical system 10.

Furthermore, in the illumination optical system 10 of the present embodiment, the condenser lens 17 includes a TIRF-SIM mode condenser lens 17A and a TIRF mode condenser lens 17B, and these condenser lenses 17A and 17B are interchangeable.

Moreover, in the illumination optical system 10 of the present embodiment, the lens 21 includes a TIRF-SIM mode lens 21A and a TIRF mode lens 21B, and these lenses 21A and 21B are interchangeable.

In other words, in TIRF-SIM mode (FIG. 14), the light-collecting optical system includes the condenser lens 17A, the lens 21A, and the field lens 23. Meanwhile, in TIRF mode (FIG. 15), the light-collecting optical system includes the condenser lens 17B, the lens 21B, and the field lens 23. (The field lens 23 is used in both modes of the light-collecting optical system.)

As illustrated in FIG. 14, in TIRF-SIM mode, the ±first-order diffracted light produced by the diffraction grating 16 behaves in the same manner as in Embodiment 1, and therefore the focused light spots formed on the pupil plane 32 by the ±first-order diffracted light fall within the TIRF region (see FIG. 8B).

Meanwhile, as illustrated in FIG. 15, in TIRF mode the output end of the optical fiber 11 (which functions as a secondary source of laser light) is shifted away from the optical axis O, and the distance from the optical axis O to this secondary light source is adjusted such that the laser light emitted from the secondary light source forms focused light spots in the TIRF region (see FIG. 8B). Note that in TIRF mode, the beam selection member 20 is set to a rotation angle at which the laser light traveling towards the TIRF region (see FIG. 8B) is not impeded.

Figure 16:
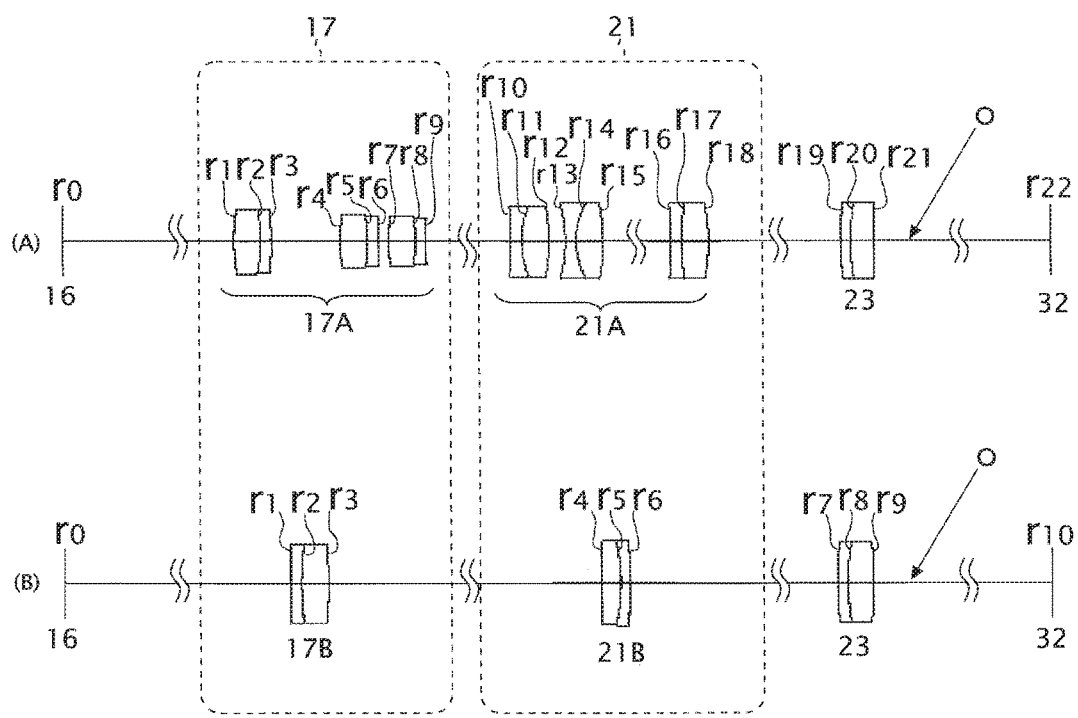
FIG. 16A illustrates the configuration of a TIRF-SIM mode light-collecting optical system (lenses 17A, 21A, and 23) of Embodiment 2.
FIG. 16B illustrates the configuration of a TIRF mode light-collecting optical system (lenses 17B, 21B, and 23) of Embodiment 2.

FIG. 16A illustrates the configuration of the light-collecting optical system (the lenses 17A, 21A, and 23) in TIRF-SIM mode, and FIG. 16B illustrates the configuration of the light-collecting optical system (the lenses 17B, 21B, and 23) in TIRF mode.

As illustrated in FIG. 16A, the TIRF-SIM mode lenses 17A and 21A each include three cemented lenses. As illustrated in FIG. 16B, the TIRF mode lenses 17B and 21B each include a single cemented lens.

The diffraction grating 16 is used in TIRF-SIM mode, and therefore assuming that there is no aberration in the light-collecting optical system, the phenomenon illustrated in FIG. 8 occurs (that is, the diffraction angle changes when the wavelength is changed). Therefore, in TIRF-SIM mode the chromatic aberration of magnification of the overall light-collecting optical system (the lenses 17A, 21A, and 23) is set such that conditional expression (2) is satisfied regardless of the wavelength used λ.

Meanwhile, the diffraction grating 16 is not used in TIRF mode, and therefore assuming that there is no aberration in the light-collecting optical system, the phenomenon illustrated in FIG. 8 does not occur (that is, the diffraction angle does not change when the wavelength is changed). Therefore, in TIRF mode the chromatic aberration of magnification of the overall light-collecting optical system (the lenses 17B, 21B, and 23) should simply be kept as small as possible.

As a result, the structured illumination microscope device 1 according to the present embodiment makes it possible to keep the TIRF condition satisfied in both TIRF-SIM mode and TIRF mode regardless of the wavelength λ used in each mode.

FIG. 17 is a table of lens data for the TIRF-SIM mode light-collecting optical system (the lenses 17A, 21A, and 23) of the present embodiment, and FIG. 18 is a correspondence table of conditions for the TIRF-SIM mode light-collecting optical system (the lenses 17A, 21A, and 23) of the present embodiment.

As shown in the first, second, and third rows from the bottom in FIG. 18, in TIRF-SIM mode each of the chromatic aberrations of magnification dY(405), dY(436), dY(486), dY(588), and dY(656) satisfy conditional expression (2).

Therefore, the TIRF-SIM mode light-collecting optical system (the lenses 17A, 21A, and 23) of the present embodiment makes it possible to keep the TIRF condition satisfied even when the wavelength used λ is switched between 405 nm, 436 nm, 486 nm, 588 nm, and 656 nm.

The distances from the optical axis O to the focused light spots on the pupil plane 32 for each wavelength are as follows.

For a wavelength of 405 nm, the distance is 2.97 mm. For a wavelength of 436 nm, the distance is 2.80 mm. For a wavelength of 486 nm, the distance is 2.71 mm. For a wavelength of 588 nm, the distance is 2.82 mm. For a wavelength of 656 nm, the distance is 2.98 mm.

Therefore, the distance from the optical axis O to the focused light spots remains greater than or equal to a prescribed value (greater than or equal to 2.71 mm) and also remains within a prescribed range (within a range of 2.71 to 2.98 mm) even when the wavelength used λ is switched between 405 nm, 436 nm, 486 nm, 588 nm, and 656 nm (within a wavelength range of 2400 to 0.700 nm).

In other words, in the present embodiment the chromatic aberration of magnification of the light-collecting optical system is adjusted such that for light in a wavelength range of ≈400 to ≈700 nm, the distance from the optical axis O to the focused light spots remains greater than or equal to a prescribed value (greater than or equal to 2.71 mm), and the change in that distance for different wavelengths remains less than or equal to a prescribed value (less than or equal to ≈0.5 mm).

Therefore, in the present embodiment the two wavelengths λ1 and λ2 emitted by the laser unit 100 in TIRF-SIM mode may be set to any two of the wavelengths 405 nm, 436 nm, 486 nm, 588 nm, and 656 nm.

Furthermore, the TIRF-SIM mode light-collecting optical system (the lenses 17A, 21A, and 23) of the present embodiment has prescribed chromatic aberrations of magnification (the third row from the bottom in FIG. 18) so that the TIRF condition remains satisfied regardless of the wavelength used λ. Meanwhile, as shown in FIG. 19, the axial chromatic aberrations of this light-collecting optical system (the lenses 17A, 21A, and 23) stay within a range of −0.105 to +0.019 mm (≈0.15 mm).

Therefore, when the structured illumination microscope device 1 according to the present embodiment is used in TIRF-SIM mode, the focus of the light-collecting optical system (the lenses 17A, 21A, and 23) does not necessarily have to be adjusted when the wavelength used λ is switched.

However, if the axial chromatic aberration of the TIRF-SIM mode light-collecting optical system (the lenses 17A, 21A, and 23) cannot be ignored, the focus may be adjusted in TIRF-SIM mode when the wavelength used λ is switched.

The focus can be adjusted by adjusting the position of the output end of the optical fiber 11 in the optical axis O direction using the position adjusting mechanism 11A or by adjusting the position of at least one of the lenses 17A, 21A, and 23 in the optical axis O direction.

Moreover, when adjusting the focus by adjusting the position of one of the lenses in the optical axis O direction, the position of the diffraction grating 16 in the optical axis O direction may also be adjusted as necessary.

FIG. 20 is a table of lens data for the TIRF mode light-collecting optical system (the lenses 17B, 21B, and 23) of the present embodiment, and FIG. 21 is a table of the chromatic aberrations of magnification of the TIRF mode light-collecting optical system (the lenses 17B, 21B, and 23) of the present embodiment.

As shown in FIG. 21, in TIRF mode the chromatic aberrations of magnification dY(405), dY(436), dY(486), dY(588), and dY(656) stay within an extremely narrow range of −0.0012 to +0.0031 mm. In other words, the chromatic aberration of magnification in TIRF mode is approximately equal to zero.

Therefore, the TIRF mode light-collecting optical system (the lenses 17B, 21B, and 23) of the present embodiment makes it possible to keep the TIRF condition satisfied even when the wavelength used λ is switched between 405 nm, 436 nm, 486 nm, 588 nm, and 656 nm.

Here, assume that the position of the optical fiber is adjusted such that the distance from the optical axis O to the focused light spots on the pupil plane 32 is 2.7 mm when the wavelength used λ is 561 nm. In this case, the distances from the optical axis O to the focused light spots for each wavelength are as follows.

For a wavelength of 405 nm, the distance is 2.7031 mm. For a wavelength of 436 nm, the distance is 2.7002 mm. For a wavelength of 486 nm, the distance is 2.6988 mm. For a wavelength of 588 nm, the distance is 2.7 mm. For a wavelength of 656 nm, the distance is 2.7014 mm.

Therefore, the distance from the optical axis O to the focused light spots remains greater than or equal to a prescribed value (greater than or equal to 2.6988 mm) and also remains within a prescribed range (within a range of 2.6988 to 2.7031 mm—that is, within a range of 2.7+0.0031 to 2.7−0.0012 mm) even when the wavelength used λ is switched between 405 nm, 436 nm, 486 nm, 588 nm, and 656 nm (within a wavelength range of ≈400 to ≈700 nm).

In other words, in the present embodiment the chromatic aberration of magnification of the light-collecting optical system is adjusted such that for light in a wavelength range of ≈400 to ≈700 nm, the distance from the optical axis O to the focused light spots remains greater than or equal to a prescribed value (greater than or equal to 2.6988 mm), and the change in that distance for different wavelengths remains less than or equal to a prescribed value (less than or equal to ≈0.01 mm).

Therefore, in the present embodiment the two wavelengths λ1 and λ2 emitted by the laser unit 100 in TIRF mode may be set to any two of the wavelengths 405 nm, 436 nm, 486 nm, 588 nm, and 656 nm.

Furthermore, as shown in FIG. 22, the axial chromatic aberrations of the TIRF mode light-collecting optical system (the lenses 17B, 21B, and 23) of the present embodiment stay within a range of −0.192 to +0.184 mm (≈0.4 mm).

Therefore, when the structured illumination microscope device 1 according to the present embodiment is used in TIRF mode, the focus of the light-collecting optical system (the lenses 17B, 21B, and 23) does not necessarily have to be adjusted when the wavelength used λ is switched.

However, if the axial chromatic aberration of the TIRF mode light-collecting optical system (the lenses 17B, 21B, and 23) cannot be ignored, the focus may be adjusted in TIRF mode when the wavelength used λ is switched.

The focus can be adjusted by adjusting the position of the output end of the optical fiber 11 in the optical axis O direction using the position adjusting mechanism 11A or by adjusting the position of at least one of the lenses 17B, 21B, and 23 in the optical axis O direction.

Moreover, when adjusting the focus by adjusting the position of one of the lenses in the optical axis O direction, the position of the diffraction grating 16 in the optical axis O direction may also be adjusted as necessary.

In the present embodiment, the laser unit 100 can emit two wavelengths of laser light. However, the number of wavelengths of laser light that can be emitted by the laser unit 100 may also be set to three or more. In this case, the three wavelengths of laser light emitted by the laser unit 100 may be set to any three of the wavelengths 405 nm, 436 nm, 486 nm, 588 nm, and 656 nm.

Furthermore, in the present embodiment the wavelengths of laser light that can be emitted by the laser unit 100 are selected from the wavelengths 405 nm, 436 nm, 486 nm, 588 nm, and 656 nm. However, any wavelengths in the range of 405 to 656 nm may be selected. This is because the TIRF-SIM mode light-collecting optical system (the lenses 17A, 21A, and 23) of the present embodiment satisfies conditional expression (2) for any wavelength in the range of 405 to 656 nm and because the chromatic aberration of magnification of the TIRF mode light-collecting optical system (the lenses 17B, 21B, and 23) of the present embodiment is kept small for wavelengths in the range of 405 to 656 nm.

Moreover, in the present embodiment the chromatic aberration of magnification of the TIRF-SIM mode light-collecting optical system (the lenses 17A, 21A, and 23) is set such that the focused light spots remain within the TIRF region regardless of the wavelength used λ in order to perform total internal reflection fluorescence (TIRF) microscopy. However, when the TIRF functionality is not needed (that is, when using the structured illumination microscope device 1 in standard SIM mode rather than TIRF-SIM mode), the focused light spots do not have to remain within the TIRF region.

In SIM mode, however, changing the distance from the optical axis O to the focused light spots by switching the wavelength used λ may also cause changes in the super-resolution effect. Therefore, it is preferable that the chromatic aberration of magnification of the light-collecting optical system (the lenses 17A, 21A, and 23) be set such that the distance from the optical axis O to the focused light spots is maintained regardless of the wavelength used λ even when TIRF functionality is not needed.

The conditional expression for this case is given below.

$$(0.75 f_o \cdot NA - af\lambda/P) \leq dY(\lambda) \leq (f_o \cdot NA - af\lambda/P),$$

where a=1 (for M=1, 2) or a=2 (for M=3)

Here, M is the number of directions in which the diffraction grating 16 has a periodic structure, λ is the wavelength used, and $dY(\lambda)$ is the chromatic aberration of magnification in the light-collecting optical system for an image of height $2f \cdot \lambda_0/P$ created by light of wavelength λ when the wavelength used λ is set to a reference wavelength $\lambda_0$. Furthermore, fo is the focal length of the objective lens 31, f is the focal length of the overall light-collecting optical system, P is the pitch of the periodic structure of the diffraction grating 16, and NA is the numerical aperture of the objective lens 31.

Satisfying this conditional expression makes it possible to achieve a super-resolution effect greater than or equal to 1.75. However, as shown in this conditional expression, the super-resolution effect for each wavelength varies from 1.75 to 2, and therefore it is preferable that the lower limit of this conditional expression be set to $(0.8 - af\lambda/P)$ in order to reduce this variation.

Furthermore, in order to switch the distance from the optical axis O to the focused light spots between a distance suitable for TIRF-SIM mode and a distance suitable for SIM mode, the diffraction grating 16 that is inserted into the light beam path may be switched between a TIRF-SIM mode diffraction grating and a SIM mode diffraction grating. The TIRF-SIM mode diffraction grating and the SIM mode diffraction grating have periodic structures of different periods.

Moreover, in the present embodiment it was assumed that the sample is irradiated with a plurality of different wavelengths of light sequentially (in order to sequentially excite a plurality of types of fluorescent regions). However, the sample may also be irradiated with a plurality of different wavelengths of light simultaneously (in order to simultaneously excite the plurality of types of fluorescent regions). In this case, it is preferable that the structured illumination microscope device 1 include a feature for separating and detecting the plurality of different wavelengths of fluorescent light.

Embodiment 3

Next, a structured illumination microscope device according to Embodiment 3 of the present invention will be described.

The structured illumination microscope device according to the present embodiment is a modification example of the structured illumination microscope device according to Embodiment 1, and therefore the following description focuses on the differences between the present embodiment and Embodiment 1.

In Embodiment 1, the light-collecting optical system is given a prescribed chromatic aberration of magnification in order to reduce changes in the distance from the optical axis O to the focused light spots on the pupil plane of the objective lens (due to changes in the diffraction angle) when switching between wavelengths. However, in the present embodiment, changes in the distance from the optical axis O to the focused light spots on the pupil conjugate plane of the objective lens (due to changes in the diffraction angle) are reduced when switching between wavelengths. In other words, changes in the distance from the optical axis O to the focused light spots on the plane in which a beam selection member is arranged (due to changes in the diffraction angle) are reduced when switching between wavelengths.

This scheme makes it possible to use standard aberration-corrected lenses for the group of lenses downstream of the light beam path selection member, thereby making it possible for the illumination device of the structured illumination microscope to be switched between a structured illumination device and another illumination device (such as a standard epi-illumination device). This scheme also has an advantage in terms of system configuration, in that the other illumination device (such as an epi-illumination device) can share some of the components of the structured illumination device.

Figure 24:
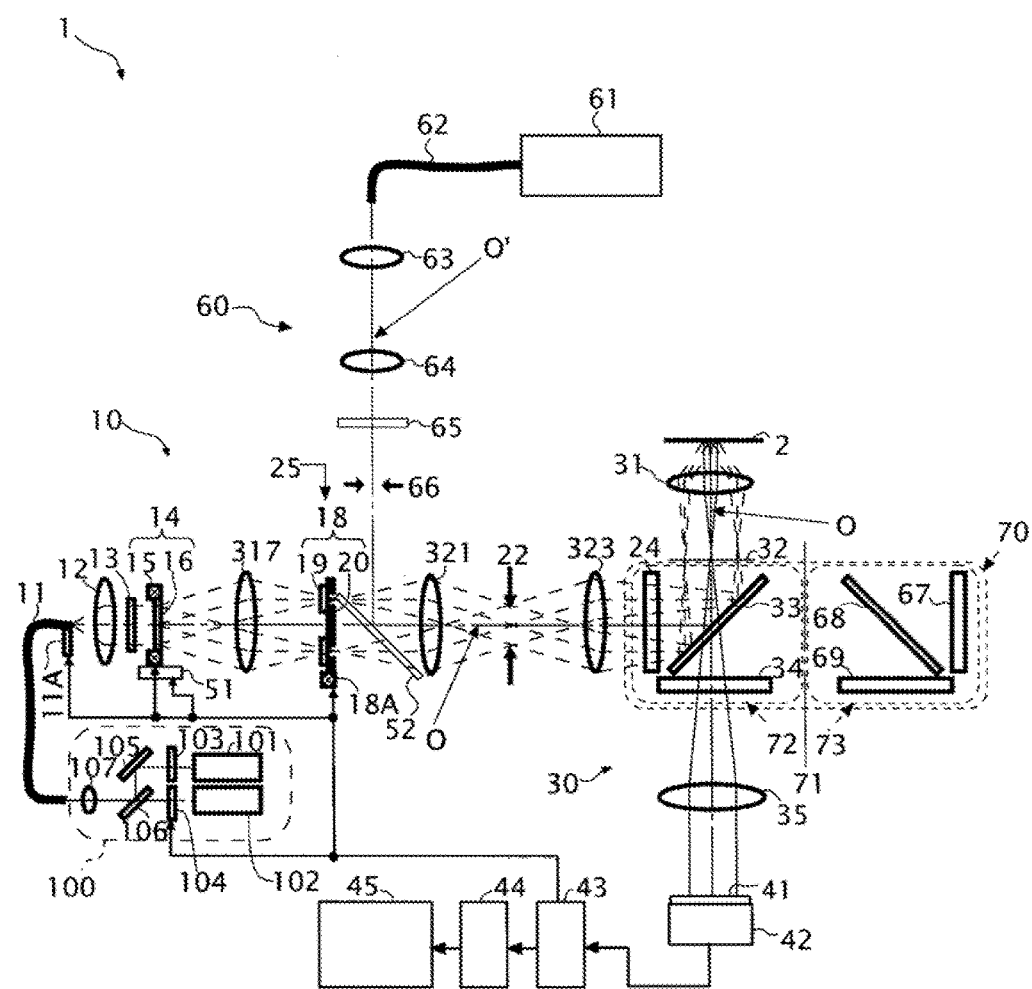
FIG. 24 illustrates the configuration of a structured illumination microscope device according to Embodiment 3.

FIG. 24 illustrates the configuration of a structured illumination microscope device 1 according to the present embodiment. In FIG. 24, components with the same functions as components illustrated in FIG. 1 are indicated using the same reference characters as in FIG. 1.

As illustrated in FIG. 24, the diffraction grating 16 and the translation mechanism 15 of the light beam splitter 14 are arranged on a uniaxial stage 51, and the position of the uniaxial stage 51 can be adjusted in the optical axis O direction. The control device 43 controls the amount by which this uniaxial stage 51 moves the diffraction grating 16 and the translation mechanism 15 in the optical axis O direction.

Furthermore, in the present embodiment a mirror 52 is placed in the light beam path between the beam selector 18 and a lens 321, and this mirror 52 can be inserted into and removed from the light beam path. When the mirror 52 is inserted into the light beam path, the illumination device of the structured illumination microscope 1 functions as a standard epi-fluorescent illumination device rather than as a structured illumination device.

Moreover, the functions of the lens 317, the lens 321, and the field lens 323 illustrated in FIG. 24 are equivalent, respectively, to the functions of the lens 17, the lens 21, and the field lens 23 in Embodiment 1. However, these lenses are given different reference characters because the correction applied to the chromatic aberration of magnification in the present embodiment is different than the correction applied to the chromatic aberration of magnification in Embodiment 1.

The epi-fluorescent illumination device 60 illustrated in FIG. 24 includes a fiber light source device 61 in which a mercury lamp functions as the light source, a second optical fiber 62, a collector lens 63, a relay lens 64, an ND filter 65, and an aperture diaphragm 66.

The light from the fiber light source device 61 functions as illumination light and is guided to the optical axis O' of the epi-fluorescent illumination device 60 by the second optical fiber 62. This illumination light is converted to parallel light by the collector lens 63 and then passes through the relay lens 64, thereby forming a light source image at the position at which the aperture diaphragm 66 is arranged. The ND filter 65 of the epi-fluorescent illumination device 60 is used to adjust the brightness of the epi-fluorescent illumination device 60.

The illumination light from the epi-fluorescent illumination device 60 reflects off of the mirror 52 and then passes through the lens 321, the field diaphragm 22, the field lens 323 and the excitation filter 24. The light then reflects off of the dichroic mirror 33, forms a light source image (the image of the output end of the second optical fiber 62) on the pupil plane 32 of the objective lens 31, and travels through the objective lens 31 to illuminate the sample 2 uniformly. In other words, the epi-fluorescent illumination device 60 uses the lens 321 and the field lens 323 of the structured illumination device (the illumination optical system 10) in order to illuminate the sample 2 uniformly.

Illuminating the sample 2 uniformly causes the fluorescent regions of the sample 2 to produce fluorescent light. Like in Embodiment 1, the fluorescent light produced by these fluorescent regions is converted to parallel light by the objective lens 31 and then proceeds through the dichroic mirror 33, the barrier filter 34, and the second objective lens 35 and forms a fluorescent image of the sample 2 on the imaging surface 41 of the image sensor 42.

When the wavelengths of light emitted by the first laser light source 101 and the second laser light source 102 and used in the illumination optical system 10 are different from the wavelength of light emitted by the fiber light source device 61 and used in the epi-fluorescent illumination device 60, the structured illumination microscope 1 may be configured as follows.

A fluorescent light cube 72 that includes the excitation filter 24, the dichroic mirror 33, and the barrier filter 34 is prepared, and another fluorescent light cube 73 that separates different wavelengths of light than the fluorescent light cube 72 is prepared. These fluorescent light cubes 72 and 73 are mounted on a fluorescent light cube turret 70. The fluorescent light cube turret 70 can rotate about a prescribed axis 71. The fluorescent light cube turret 70 rotates about the axis 71 by prescribed angles to switch the fluorescent light cube that is placed on the optical axis O of the objective lens 31 between the fluorescent light cubes 72 and 73.

Moreover, aberration-corrected lenses similar to those typically used in the epi-fluorescent illumination devices of inverted microscopes are used for the lenses of the epi-fluorescent illumination device 60 (that is, for the collector lens 63 and the relay lens 64). In addition, aberration-corrected lenses (that is, lenses in which the chromatic aberration of magnification is substantially equal to 0) similar to those typically used in the epi-fluorescent illumination devices of inverted microscopes are also used for the lenses used by the epi-fluorescent illumination device 60 to produce epi-illumination light (that is, for the lens 321 and the field lens 323).

Therefore, in contrast to Embodiment 1, in which the chromatic aberration of magnitude of the overall light-collecting optical system (the lenses 17, 21, and 23) was set to correct changes in the position of the focused light spots on the pupil plane due to changes in the diffraction angle when switching between wavelengths, in the present embodiment only the chromatic aberration of magnification of the lens 317 of the light-collecting optical system (the lenses 317, 321, and 323) rather than the chromatic aberration of magnification of the overall light-collecting optical system needs to be set. Next, the details of this configuration will be described.

In the present embodiment, like in Embodiment 1, the equation that must be satisfied to keep the TIRF condition satisfied is given by equation (2).

$$(fo \cdot nw - af\lambda/P) \leq dY(\lambda) \leq (fo \cdot NA - af\lambda/P), \quad (2)$$

where a=1 (for M=1, 2) or a=2 (for M=3)

Here, $dY(\lambda)$ is the chromatic aberration of magnification in the light-collecting optical system for an image of height $2f \cdot \lambda_0/P$ created by light of wavelength $\lambda$ when the wavelength used $\lambda$ is set to a reference wavelength $\lambda_0$. Furthermore, fo is the focal length of the objective lens 31, f is the focal length of the overall light-collecting optical system (the lenses 317, 321, and 323), P is the pitch of the periodic structure of the diffraction grating 16, NA is the numerical aperture of the objective lens 31, M is the number of directions in which the diffraction grating 16 has a periodic structure, and nw is the refractive index of the sample 2.

Figures 25, 26:
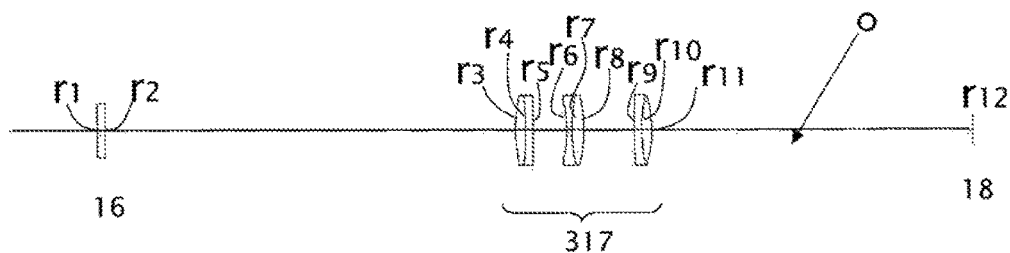
FIG. 25 illustrates the configuration of a lens 317 of Embodiment 3.
FIG. 26 is a table of lens data for the lens 317.

FIG. 25 illustrates the configuration of the lens 317 of the present embodiment. As illustrated in FIG. 25, the lens 317 of the present embodiment has a 3-group, 6-element configuration. $r_1$ and $r_2$ are the optical surfaces of the diffraction grating 16. The optical surface $r_1$ is a plane-parallel plate in which step shapes are formed to make the optical surface $r_1$ function as a diffraction grating. The reason that unlike in Embodiments 1 and 2, the lens 317 has a 3-group configuration in the present embodiment is because only the lens 317 is used to set the chromatic aberration of magnification needed for the light-collecting optical system.

FIG. 26 is a table of lens data for the lens 317. FIG. 27 is a table that gives the distance from the optical axis O to the light beams on the plane in which the beam selection member 20 is arranged (the pupil conjugate plane) for each wavelength of light (this distance is determined by the power of the lens 317), the focal lengths of the lens 321 and the field lens 323, the projection magnification from the plane in which the beam selection member 20 is arranged to the pupil plane 32, and the distance from the optical axis O to the focused light spots formed on the pupil plane 32 of the objective lens 31.

Note that the light beam selector 18 is conjugate to the pupil plane 32 of the objective lens 31, and the projection magnification from the plane in which the beam selection member 20 is arranged to the pupil plane 32 is the ratio of the powers of the lens 321 and the field lens 323.

FIG. 28 is a correspondence table of conditions for the light-collecting optical system (the lenses 317, 321, and 323) of the present embodiment.

In the present embodiment, the wavelength of the first laser light source 101 may be set to 486 nm, and the second laser light source 102 may include a laser light source with a wavelength of 405 nm and a laser light source with a wavelength of 436 nm.

Therefore, here the reference wavelength $\lambda_0$ is set to 486 nm, and the wavelength used $\lambda$ can be switched between 405 nm and 436 nm. In FIG. 28, the third row from the bottom gives the chromatic aberrations of magnification dY(405) and dY(436) for light of wavelengths 405 nm and 436 nm, respectively.

As shown in the first and second rows from the bottom in FIG. 28, these chromatic aberrations of magnification dY(405) and dY(436) both satisfy conditional expression (2).

Therefore, the light-collecting optical system (the lenses 317, 321, and 323) of the present embodiment makes it possible to keep the focused light spots formed on the pupil plane 32 of the objective lens 31 by the ±first-order diffracted light produced by the diffraction grating 16 within the TIRF region (that is, keep the TIRF condition satisfied) even when the wavelength used $\lambda$ is switched between 405 nm, 436 nm, and 486 nm.

As shown in FIG. 27, the distance from the optical axis to the focused light spots on the pupil plane 32 remains substantially constant for each wavelength of light (this distance remains within a range of 2.85 to 2.88 mm). In other words, the changes in the distance to the focused light spots remain sufficiently within a range of less than or equal to ≈0.5 mm, and the chromatic aberration of magnification is adjusted such that these changes are substantially equal to zero.

Therefore, in the structured illumination microscope device 1 according to the present embodiment, the two wavelengths $\lambda 1$ and $\lambda 2$ emitted by the laser unit 100 may be set to any two of the wavelengths 405 nm, 436 nm, and 486 nm.

Furthermore, as illustrated in FIG. 29, because the light-collecting optical system (the lenses 317, 321, and 323) of the present embodiment has a prescribed chromatic aberration of magnification (given by the third row from the bottom in FIG. 28), the light-collecting optical system also exhibits axial chromatic aberration. FIG. 29 shows the axial chromatic aberration of the lens 317 at the plane in which the beam selection member 20 is arranged (the pupil conjugate plane) and the axial chromatic aberration of the lens 317 at the plane in which the light beam splitter 14 is arranged (as calculated by tracing the light beams backwards).

Therefore, in the structured illumination microscope device 1 according to the present embodiment, two focuses have to be adjusted when the wavelength used $\lambda$ is switched.

The first focus adjustment is for adjusting the position in the optical axis direction at which the light is focused on the pupil plane 32, and this focus can be adjusted by adjusting the position of the output end of the optical fiber 11 in the optical axis direction using the position adjusting mechanism 11A. The actual amount by which the output end of the optical fiber 11 should be moved is calculated by multiplying the distances listed in FIG. 29 by the reciprocal of the axial magnification of the components of the optical system from the output end of the optical fiber 11 to the light beam selector 18.

The second focus adjustment is for adjusting the interference fringes (the structured illumination) formed on the sample 2, and this focus can be adjusted by driving the uniaxial stage 51 on which the light beam splitter 14 is mounted in order to adjust the position of the diffraction grating 16 in the optical axis direction. The actual amount by which the uniaxial stage 51 should be moved is the same as the distances listed in FIG. 29.

Moreover, it is preferable that the amount by which these focuses should be adjusted for each wavelength be measured in advance as part of the calibration process while setting up the structured illumination microscope device 1 and then stored in the control device 43. Doing this makes it possible to speed up the focus adjustments when switching between wavelengths.

In the present embodiment, the chromatic aberration of magnification of the lens 317 of the light-collecting optical system is set such that the focused light spots remain within the TIRF region regardless of the wavelength used $\lambda$ in order to perform total internal reflection fluorescence (TIRF) microscopy. However, like in Embodiment 1, when the TIRF functionality is not needed (that is, when using the structured illumination microscope device 1 in standard SIM mode rather than TIRF-SIM mode), the focused light spots do not have to remain within the TIRF region.

Furthermore, like the structured illumination microscope devices 1 according to Embodiments 1 and 2, the structured illumination microscope device 1 of the present embodiment may be modified as appropriate.

Modification Examples of the Embodiments

In the embodiments described above, the half-wave plate 19 that can be rotated about the optical axis is used to keep the ±first-order diffracted beams incident on the sample 2 s-polarized. However, a fixed quarter-wave plate and a quarter-wave plate that can be rotated about the optical axis may also be used. In this case, however, the rotation angle of rotatable quarter-wave plate relative to the first reference position must be set to the same value as the rotation angle of the beam selection member 20 relative to the second reference position.

Moreover, in the embodiments described above, the diffraction grating 16 in which the number of directions M in which the diffraction grating 16 has a periodic structure is at least two (that is, the diffraction grating 16 that simultaneously produces a plurality of diffracted beam groups in different splitting directions (see FIG. 2A)) is used to split the light beams emitted from the light source. However, a diffraction grating in which the number of directions M in which the diffraction grating has a periodic structure is one (that is, a diffraction grating that produces a single diffracted beam group in a single splitting direction) may also be used.

In this case, however, the diffraction grating must be rotated about the optical axis in order to switch the direction of the interference fringes. Moreover, in this case a non-rotatable zero-order light cut-off mask may be used in place of the rotatable beam selection member 20. This zero-order light cut-off mask transmits ±first-order diffracted light but blocks zero-order diffracted light and second-order and higher-order diffracted light.

In other words, in the illumination optical system 10 as described above, the diffraction unit (16) may be a diffraction grating that has a periodic structure in a single direction that is orthogonal to the optical axis, and in this case, the Illumination optical system 10 may further include a rotation unit (not illustrated in the figures) that rotates the direction in which the pair of light beams are incident on the sample (2) about the optical axis.

Furthermore, in the embodiments described above, in TIRF-SIM mode two light beams are used to form the interference fringes on the sample 2 (that is, the structured illumination microscope device 1 is used in 2D-SIM mode). However, the structured illumination microscope device 1 may also have a SIM mode in which three light beams are used to form interference fringes on the sample 2 (that is, a 3D-SIM mode).

Figure 23:
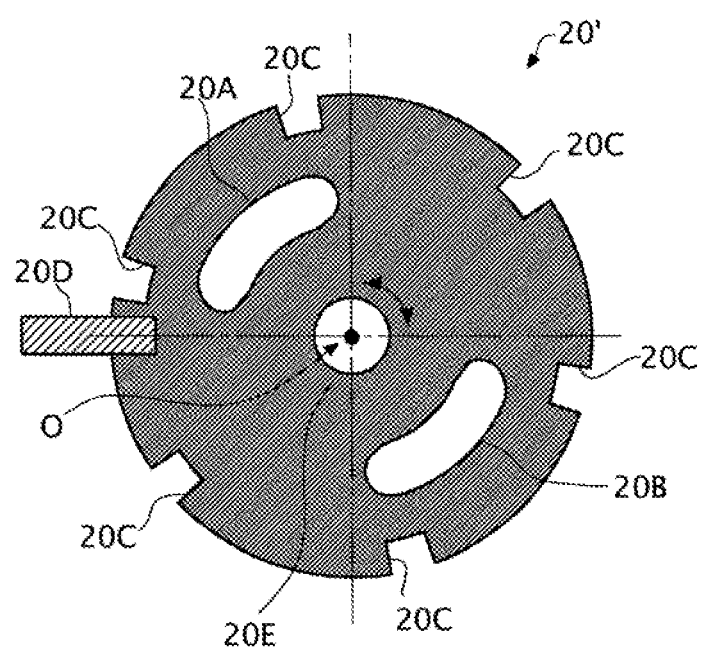
FIG. 23 illustrates a beam selection member 20' for a 3D-SIM mode.

For 3D-SIM mode, the beam selection member 20' illustrated in FIG. 23 may be used in place of the beam selection member 20 illustrated in FIG. 6. In this beam selection member 20', an additional opening 20E is formed in the beam selection member 20 illustrated in FIG. 6 in order to allow the zero-order diffracted beam to pass through. This opening 20E is formed near the optical axis and is circular, for example. Using this type of beam selection member 20' makes it possible to use not only the ±first-order diffracted beams but also the zero-order diffracted beam to form interference fringes.

In this case, the interference fringes are produced by interference of three types of diffracted beams (three-beam interference) and spatially modulate the sample 2 not only in the surface direction but also in the depth direction of the sample 2. Therefore, these interference fringes can be used to produce a super-resolution image of the sample 2 in the depth direction thereof as well.

Furthermore, in the embodiments described above, in TIRF-SIM mode the +first-order diffracted beam and the −first-order diffracted beam are used in combination as the two diffracted beams that form the structured illumination light used to form interference fringes on the sample 2. However, another combination of diffracted beams may also be used.

Furthermore, in the embodiments described above, in 3D-SIM mode the +first-order diffracted beam, the −first-order diffracted beam, and the zero-order diffracted beam are used in combination as the three diffracted beams that form the structured illumination light used to form interference fringes on the sample 2. However, another combination of diffracted beams may also be used.

When using three diffracted beams to form the interference fringes, any three types of diffracted light in which there are equal intervals between the diffraction orders may be used. Therefore, combinations such as zero-order diffracted light, first-order diffracted light, and second-order diffracted light; ±second-order diffracted light and zero-order diffracted light; and ±third-order diffracted light and zero-order diffracted light may all be used, for example.

Furthermore, the illumination optical systems 10 of Embodiments 1 to 3 are epi-illumination optical systems that use the objective lens 31. However, the illumination optical system is not limited to these examples and may be a transflective illumination optical system that uses a condenser lens in place of the objective lens 31. In this case, the focused light spots are formed on the pupil plane of the condenser lens.

Moreover, the light beam splitters of Embodiments 1 to 3 use diffraction gratings to split the light beam. Alternatively, however, a spatial light modulator (SLM) that functions as a phase diffraction grating may be used in combination with a control unit that sends drive signals to the spatial light modulator, for example. In this case, the control unit switches the drive signals sent to the spatial light modulator, thereby making it possible to quickly switch the periodic structure of the spatial light modulator (the periodic structure that functions as a diffraction grating).

Effects of the Embodiments

A structured illumination device (the laser unit 100, the optical fiber 11, and the illumination optical system 10) according to the embodiments described above includes: a diffraction unit (the diffraction grating 16) that diffracts light beams of a plurality of wavelengths that are emitted simultaneously or sequentially by a light source (the laser unit 100) into a plurality of diffracted beams; and an optical system (the illumination optical system 10) that forms interference fringes on a surface of a sample using the plurality of diffracted beams diffracted by the diffraction unit (the diffraction grating 16), the optical system (the illumination optical system 10) including a first optical system (the objective lens 31) and a second optical system (the light-collecting optical system that includes the lenses 17, 21, and 23 or the lenses 317, 321, and 323) that focuses the plurality of diffracted beams at positions on or near a pupil plane (32) of the first optical system (the objective lens 31), and a magnification characteristic $dY(\lambda)$ of the second optical system satisfying the following condition for each wavelength of the plurality of wavelengths.

$$(f o \cdot n w - a f \lambda / P) \leq d Y(\lambda) \leq (f o \cdot NA - a f \lambda / P).$$

where a=1 (for M=1, 2) or a=2 (for M=3)

Here, M is a number of directions in which the diffraction unit has a periodic structure, $\lambda$ is any wavelength of the plurality of wavelengths, $dY(\lambda)$ is a difference between an image height $2f \cdot \lambda_0/P$ where $\lambda_0$ is a reference wavelength for the plurality of wavelengths and an image height $2f \cdot \lambda/P$ where $\lambda$ is any wavelength of the plurality of wavelengths, fo is a focal length of the first optical system for the wavelength $\lambda$, f is a focal length of the second optical system for the wavelength $\lambda$, P is a pitch of the diffraction unit, NA is a numerical aperture of the first optical system, and nw is a refractive index of the wavelength $\lambda$ of the sample.

In other words, the magnification characteristics (the chromatic aberration of magnification) of the second optical system (the light-collecting optical system that includes the lenses 17, 21, and 23 or the lenses 317, 321, and 323) for each wavelength of the plurality of wavelengths are set such that the diffracted light beams of each of the plurality of wavelengths are focused at positions within a prescribed region of the pupil plane. This prescribed region is a TIRF region that allows the interference fringes to form an evanescent field near the surface of the sample.

Therefore, the structured illumination microscope device (1) according to the embodiments described above makes it possible to observe an extremely thin layer of the surface of the sample (2) at each of the plurality of wavelengths.

Moreover, the diffraction unit (the diffraction grating 16) can be inserted into or removed from a light beam path of the emitted light beams, and the second optical system (the lenses 17A, 21A, and 23) is interchangeable with another second optical system (the lenses 17B, 21B, and 23) that has different magnification characteristics.

This makes it possible to switch the structured illumination microscope device 1 according to the embodiments described above between a TIRF-SIM mode and a TIRF mode.

In the illumination optical system 10 of the embodiments described above, a component of the second optical system (the light-collecting optical system that includes the lenses 17A, 21A, and 23) to be interchanged is one of the components of the second optical system (the lenses 17A and 21A).

Keeping the number of components to be interchanged small in this way makes it possible to avoid additional complexity in the mechanism needed to interchange the components.

In the illumination optical system 10 of the embodiments described above, at least the component of the second optical system (the light-collecting optical system that includes the lenses 17A, 21A, and 23) to be interchanged (the lens 17A or 21A) includes a cemented lens.

Interchanging cemented lenses that effectively control the magnification characteristics makes it possible to reliably switch the magnification characteristics of the second optical system.

Furthermore, the structured illumination device (the laser unit 100, the optical fiber 11, and the illumination optical system 10) according to the embodiments described above may further include a control unit that switches the periodic structure of the diffraction unit (a spatial light modulator).

Moreover, the structured illumination device (the laser unit 100, the optical fiber 11, and the illumination optical system 10) according to the embodiments described above may further include a position adjusting unit (the position adjusting mechanism 11A) for adjusting a position in an optical axis direction at which the first optical system (the objective lens 31) focuses light.

This makes it possible for the structured illumination device (the laser unit 100, the optical fiber 11, and the illumination optical system 10) according to the embodiments described above to handle changes in focus when switching between the plurality of wavelengths (that is, changes in focus due to the axial chromatic aberration of the second optical system or due to the chromatic aberration of the pupil of the objective lens).

Furthermore, the illumination optical system 10 of the embodiments described above may further include a phase shifting unit (the translation mechanism 15) for shifting a phase of the interference fringes.

This makes it possible for the structured illumination microscope device 1 according to the present embodiment to reliably capture the sequence of modulated images necessary for the demodulation process.

The structured illumination device according to the embodiments described above may further include a light selection unit (the beam selection member 20) that selects a single pair of diffracted beams from the plurality of diffracted beams diffracted by the diffraction unit (the diffraction grating 16 or the spatial light modulator), and the diffraction unit (the diffraction grating 16 or the spatial light modulator) may have a periodic structure in a plurality of different directions within a plane orthogonal to an optical axis of the optical system.

Therefore, the structured illumination microscope device 1 according to the embodiments described above makes it possible to achieve the super-resolution effect in a plurality of directions.

The plurality of wavelengths may be within a range of 400 to 700 nm.

Using wavelengths in this range makes it possible to adjust the magnification characteristics of the second optical system (the light-collecting optical system that includes the lenses 17, 21, and 23) such that the distance from the optical axis (O) to the focused light spots remains substantially constant for each wavelength of the plurality of wavelengths (see FIGS. 11, 12, and 26 to 29 for specific examples).

The structured illumination device (the laser unit 100, the optical fiber 11, and the illumination optical system 10) according to the embodiments described above may further include a switching unit that inserts and removes an optical member (the mirror 52) into and from a light beam path between the diffraction unit (the diffraction grating 16) and the pupil plane in order to switch light that illuminates the surface of the sample between structured illumination light that forms interference fringes and another type of Illumination light emitted by a second light source (the fiber light source device 61) that is different from the light source (the laser unit 100).

In this way, the structured illumination device (the laser unit 100, the optical fiber 11, and the illumination optical system 10) according to the embodiments described above makes it possible to efficiently switch the state of the illumination light.

The structured illumination microscope device 1 according to the embodiments described above may include an imaging optical system (the second objective lens 35) that uses light beams observed from the sample (2) when modulated by the interference fringes to form an image on a light detector (the image sensor 42).

Furthermore, the structured illumination microscope device 1 according to the embodiments described above may further include a processing unit (the image storage/processing device 44) that generates a demodulated image of the sample (2) using images generated by the light detector (the image sensor 42).

Moreover, a structured illumination device (the laser unit 100, the optical fiber 11, and the illumination optical system 10) according to the embodiments described above includes: a diffraction unit (the diffraction grating 16) that diffracts light beams of a plurality of wavelengths that are emitted simultaneously or sequentially by a light source (the laser unit 100) into a plurality of diffracted beams; and an optical system (the Illumination optical system 10) that forms interference fringes on a surface of a sample using the plurality of diffracted beams diffracted by the diffraction unit (the diffraction grating 16), the optical system (the illumination optical system 10) including a first optical system (the objective lens 31) and a second optical system (the light-collecting optical system that includes the lenses 17, 21, and 23 or the lenses 317, 321, and 323) that focuses the plurality of diffracted beams at positions on or near a pupil plane (32) of the first optical system (the objective lens 31), and a magnification characteristic $dY(\lambda)$ of the second optical system satisfying the following condition for each wavelength of the plurality of wavelengths.

$$(0.75 fo \cdot NA - af\lambda/P) \le dY(\lambda) \le (fo \cdot NA - af\lambda/P),$$

where a=1 (for M=1, 2) or a=2 (for M=3)

Here, M is a number of directions in which the diffraction unit has a periodic structure, $\lambda$ is any wavelength of the plurality of wavelengths, $dY(\lambda)$ is a difference between an image height $2f \cdot \lambda_0/P$ where $\lambda_0$ is a reference wavelength for the plurality of wavelengths and an image height $2f \cdot \lambda/P$ where $\lambda$ is any wavelength of the plurality of wavelengths, fo is a focal length of the first optical system (the objective lens 31) for the wavelength $\lambda$, f is a focal length of the second optical system (the light-collecting optical system that includes the lenses 17, 21, and 23 or the lenses 317, 321, and 323) for the wavelength $\lambda$, P is a pitch of the diffraction unit, and NA is a numerical aperture of the first optical system (the objective lens 31).

Therefore, the structured illumination microscope device (1) according to the embodiments described above makes it possible to achieve the desired super-resolution effect for each wavelength of the plurality of wavelengths.

<Description of Demodulation Process>

Next, an example of the demodulation process will be described.

Here, assume that the structured illumination microscope device is used in 2D-SIM mode, the number of directions $M_{max}$ in which the interference fringes are formed is 1, and the number of phases used $N_{max}$ is 3.

Let x be the coordinate that represents the modulation direction on the sample, $P_r(x)$ be the point image intensity distribution of the imaging optical system, $O_r(x)$ be the structure of the fluorescent region of the sample, K be the spatial frequency (modulation frequency) of the interference fringes, $\phi$ be the phase (modulation phase) of the interference fringes, and $m_i$ be the amplitude (modulation amplitude) of the interference fringes (where I is the modulation order, which is −1, 0, or 1). In this case, the pattern (modulation waveform) of the interference fringes is given by $m_i \exp(ilKx+\phi)$, and therefore a modulated image $I_r(x)$ of the sample is given by the following formula.

$$I_r(x) = \sum_i m_i(O_i(x)\exp(ilKx + il\phi)) * P_r(x))$$

Note that the * symbol in the formula represents the convolution integral of the two quantities. Also, note that in the following description, in order to distinguish between quantities in real space and quantities in wavenumber space, quantities in real space are given the subscript "r" and quantities in wavenumber space are given the subscript "k".

Applying a Fourier transform to the modulated image Ir(x) yields the following formula ($I_k(k)$).

$$I_k(k) = \sum_i m_i \exp(i l \phi) O_k(k + IK) P_k(k))$$

Applying a Fourier transform to the point image intensity distribution $P_r(x)$ yields $P_k(k)$, which is the optical transfer function (OTF) of the imaging optical system.

The quantity $O_k(k+IK)$ (I=−1, 0, 1) in the formula represents the modulation components of each order superimposed on the modulated image $I_k(k)$. For the +first-order modulation component $O_k(k+K)$ and the −first-order modulation component (k−K), the actual spatial frequency components of the sample 2 are shifted by exactly K (towards a lower frequency). The larger the magnitude of this shift, the greater the super-resolution effect. Therefore, it is preferable that the spatial frequency of the interference fringes be set as high as possible within the range that can be imaged by the imaging optical system.

In a sequence of modulated images (that is, $N_{max} \times M_{max}$ frames of modulated image data), three frames of modulated image data produced using interference fringes of different phases differ only by $\phi$, and $m_i$ and K are constant. Therefore, letting $\phi_j$ be the phase of the interference fringes used in the jth frame of modulated image data of those three frames, the modulated image $I_{kj}(k)$ for that jth frame is given by the following formula.

$$I_{kj}(k) = \sum_i m_i \exp(i l \phi_j) O_k(k + IK) P_k(k))$$

In the demodulation process, the formula above is applied to obtain the modulated images for the three frames, and the resulting system of three equations is solved to make the modulation components of each order $O_k(k+IK)$ (I=−1, 0, 1) known (that is, to separate these components). Note that the quantity $P_k(k)$ in this formula is a characteristic quantity of the imaging optical system and can be measured in advance.

Once the modulation components of each order $O_k(k+IK)$ (I=−1, 0, 1) are separated, the quantities $O_k(k+IK)P_k(k)$ (I=−1, 0, 1) become known and may be divided by $P_k(k)$. Alternatively, instead of simple division, a well-known technique such as a Wiener filter that is less susceptible to the effects of noise may be used.

Furthermore, the ±first-order modulation components $O_k(k+K)$ and $O_k(k-K)$ are shifted (rearranged) in the x direction by exactly the modulation frequency K, and therefore in the demodulation process, the modulation components of each order $O_k(k+IK)$ (I=−1, 0, 1) can be weighted and combined in wavenumber space to generate a demodulated image $O_k(x)$ with a wide frequency range.

Applying an inverse Fourier transform to this demodulated image $O_k(\lambda)$ yields a super-resolution image $O_r(x)$ of the sample 15. This super-resolution image $O_r(x)$ has a high super-resolution in the modulation direction of the interference fringes (the x direction).

Next, assume that the number of directions $M_{max}$ in which the interference fringes are formed is 3, and the number of phases $N_{max}$ used for each direction is 3.

Figure 30:
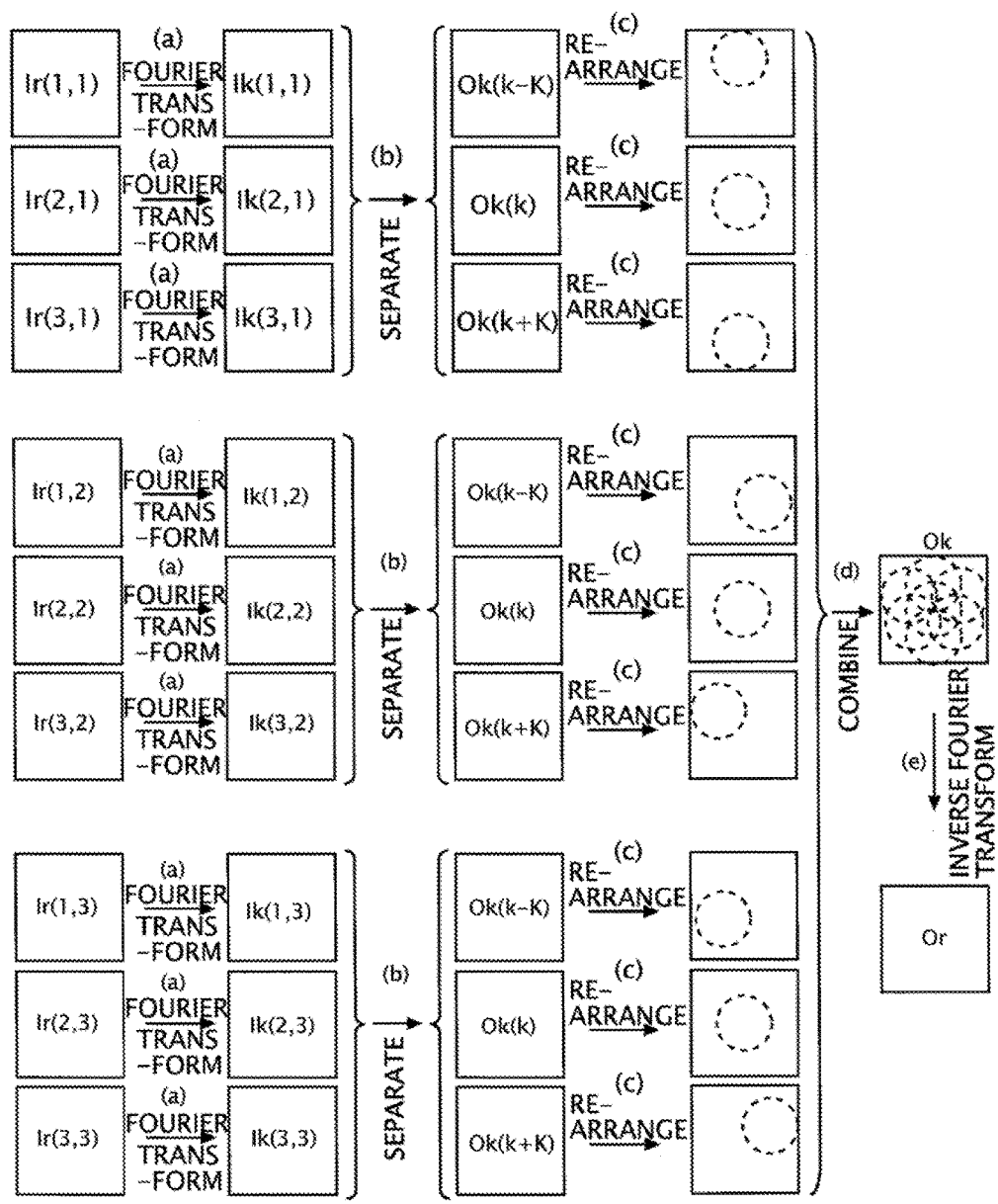
FIG. 30 illustrates a demodulation process for when the number of phases used $N_{max}$=3 and the number of directions $M_{max}$=3.

FIG. 30 illustrates the demodulation process for when the number of phases used $N_{max}$=3 and the number of directions $M_{max}$=3. In FIG. 30, the reference characters $I_r(1, 1)$, $I_r(2, 1)$, . . . , $I_r(3, 3)$ represent modulated images formed using interference fringes with different combinations of phases and directions. For a modulated image $I_r(N, M)$, N is a number representing the phase of the interference fringes used to form the modulated image, and M is a number representing the direction of the interference fringes used to form the modulated image.

As illustrated in FIG. 30, in the demodulation process for when the number of phases used $N_{max}$=3 and the number of directions $M_{max}$=3, Fourier transforms are applied separately to 3×3=9 frames of modulated image data (FIG. 30(*a*)). Next, for the modulated images formed using interference fringes of the same direction, the modulation components are separated (FIG. 30(*b*)), and the resulting 9 modulation components are each rearranged (FIG. 30(*c*)).

Then, the modulation components in the same wavenumber space are weighted and combined (FIG. 30(d)) to generate a demodulated image $O_k$ with a wide frequency range in three directions. Applying an inverse Fourier transform to this demodulated image $O_k$ yields a super-resolution image $O_r$ of the sample 15. This super-resolution image $O_r$ has a high super-resolution in each of the three directions.

As illustrated in FIG. 30, when $N_{max}=3$ and $M_{max}=3$, one frame of super-resolution image data $O_r$ is generated from $N_{max} \times M_{max}=9$ frames of modulated image data.

Here, it was assumed that the number of phases used $N_{max}$ was equal to 3, and the resulting system of equations was solved to separate the modulation components. When the number of phases used $N_{max}$ is greater than 3, the method disclosed in Patent Document 2: WO 2006/109448 may be used.

Furthermore, the description above assumes the structured illumination microscope device is used in 2D-SIM mode. For 3D-SIM mode, five modulation components are superimposed on the modulated image—the −second-order modulation component, the −first-order modulation component, the zero-order modulation component, the +first-order modulation component, and the +second-order modulation component (that is, I=−2, −1, 0, +1, +2)—and therefore these modulation components should be separated. Therefore, in 3D-SIM mode, the number of phases used $N_{max}$ should be greater than or equal to 5, and the number of frames in the sequence of modulated image data should be increased.

Moreover, here the rearrangement process (FIG. 30(c)) and the combination process (FIG. 30(d)) are performed sequentially in the demodulation process, but it is also possible to perform both of these processes at once. To do this, a method such as formula (1) in Online Methods in Non-Patent Document 1: "Super-Resolution Video Microscopy of Live Cells by Structured Illumination", Peter Kner, Bryant B. Chhun, Eric R. Griffis, Lukman Winoto, and Mats G. L. Gustafsson, NATURE METHODS Vol. 6 NO. 5, pp. 339-342, (2009) may be used.

ADDITIONAL NOTES

Note that various aspects of the embodiments described above may be combined as appropriate. Moreover, some of the component parts may be removed. Moreover, to the extent permissible by law, all publications and US patent documents related to the devices or the like used in the embodiments and modification examples as described above are incorporated herein by reference.

The many features and advantages of the embodiments are apparent from the detailed specification and, thus, it is intended by the appended claims to cover all such features and advantages of the embodiments that fall within the true spirit and scope thereof. Further, since numerous modifications and changes will readily occur to those skilled in the art, it is not desired to limit the inventive embodiments to the exact construction and operation illustrated and described, and accordingly all suitable modifications and equivalents may be resorted to, falling within the scope thereof.

What is claimed is:

1. A structured illumination device, comprising:
a diffraction member that diffracts light emitted by a light source which emits a plurality of wavelengths simultaneously or sequentially; and
an optical system that forms interference fringes on a surface of a sample by interfering at least a part of diffracted light diffracted by the diffraction member, the optical system including a first optical system and a second optical system that focuses at least a part of the diffracted light on or near a pupil plane of the first optical system, and
a magnification characteristic $dY(\lambda)$ of the second optical system satisfying the following condition for each wavelength of the plurality of wavelengths:

$$(fo \cdot nw - af\lambda/P) \leq dY(\lambda) \leq (fo \cdot NA - af\lambda/P),$$

where a=1 (for M=1, 2) or a=2 (for M=3), M is a number of directions in which the diffraction member has a periodic structure, $\lambda$ is any wavelength of the plurality of wavelengths, $dY(\lambda)$ is a difference between an image height $2f \cdot \lambda_0/P$ where $\lambda_0$ is a reference wavelength for the plurality of wavelengths and an image height $2f \cdot \lambda/P$ where $\lambda$ is any wavelength of the plurality of wavelengths, fo is a focal length of the first optical system for the wavelength $\lambda$, f is a focal length of the second optical system for the wavelength $\lambda$, P is a pitch of the diffraction member, NA is a numerical aperture of the first optical system, and nw is a refractive index of the wavelength $\lambda$ of the sample.

2. The structured illumination device according to claim 1,
wherein the diffraction member can be inserted into or removed from a light beam path, and
wherein the second optical system is interchangeable with another second optical system that has different magnification characteristics.

3. The structured illumination device according to claim 2, wherein a component of the second optical system to be interchanged is one of the components of the second optical system.

4. The structured illumination device according to claim 3, wherein at least the component of the second optical system to be interchanged includes a cemented lens.

5. The structured illumination device according to claim 3, further comprising:
a control unit that switches the periodic structure of the diffraction member.

6. The structured illumination device according to claim 2, wherein at least the component of the second optical system to be interchanged includes a cemented lens.

7. The structured illumination device according to claim 6, further comprising:
a control unit that switches the periodic structure of the diffraction member.

8. The structured illumination device according to claim 2, further comprising:
a control unit that switches the periodic structure of the diffraction member.

9. The structured illumination device according to claim 1, further comprising:
a control unit that switches the periodic structure of the diffraction member.

10. The structured illumination device according to claim 1, further comprising:
a position adjusting unit for adjusting a position at which at least a part of the diffracted light is focused in an optical axis direction of the first optical system.

11. The structured illumination device according to claim 1, further comprising:
a phase shifting unit for shifting a phase of the interference fringes.

12. The structured illumination device according to claim 1, further comprising:

a light selection unit that selects a diffracted light in a predetermined direction from the diffracted light in a plurality of directions diffracted by the diffraction member, wherein the diffraction member has a periodic structure in a plurality of different directions within a plane orthogonal to an optical axis of the optical system.

13. The structured illumination device according to claim 1, further comprising:

a rotation unit that rotates the diffracted light about an optical axis, wherein the diffraction member has a periodic structure in a single direction within a plane orthogonal to the optical axis of the optical system.

14. The structured illumination device according to claim 1, wherein the plurality of wavelengths are within a range of 400 to 700 nm.

15. The structured illumination device according to claim 1, further comprising:

a switching unit that inserts and removes an optical member into and from a light beam path between the diffraction member and the pupil plane in order to switch light that illuminates a sample between structured illumination light that forms interference fringes and another type of illumination light emitted by a second light source that is different from the light source.

16. A structured illumination microscope device, comprising:

the structured illumination device described in claim 1; and an imaging optical system that uses light observed from the sample when modulated by the interference fringes to form an image on a light detector.

17. The structured illumination microscope device according to claim 16, further comprising:

a processing unit that generates a demodulated image of the sample using images generated by the light detector.

18. A structured illumination device, comprising:

a diffraction member that diffracts light emitted by a light source which emits light of a plurality of wavelengths simultaneously or sequentially; and an optical system that forms interference fringes on a surface of a sample by interfering at least a part of a diffracted light diffracted by the diffraction member, the optical system including a first optical system and a second optical system that focuses the at least a part of the diffracted light on or near a pupil plane of the first optical system, and a magnification characteristic $dY(\lambda)$ of the second optical system satisfying the following condition for each wavelength of the plurality of wavelengths:

$$(0.75 fo \cdot NA - af\lambda/P) \leq dY(\lambda) \leq (fo \cdot NA - af\lambda/P),$$

where a=1 (for M=1, 2) or a=2 (for M=3), M is a number of directions in which the diffraction memeber has a periodic structure, $\lambda$ is any wavelength of the plurality of wavelengths, $dY(\lambda)$ is a difference between an image height $2f \cdot \lambda_0/P$ where $\lambda_0$ is a reference wavelength for the plurality of wavelengths and an image height $2f \cdot \lambda/P$ where $\lambda$ is any wavelength of the plurality of wavelengths, fo is a focal length of the first optical system for the wavelength $\lambda$, f is a focal length of the second optical system for the wavelength $\lambda$, P is a pitch of the diffraction member, and NA is a numerical aperture of the first optical system.

* * * * *